(12) United States Patent
Endo

(10) Patent No.: US 7,313,219 B2
(45) Date of Patent: Dec. 25, 2007

(54) RADIATION IMAGE PICK-UP DEVICE, RADIATION IMAGE PICK-UP METHOD AND PROGRAM

(75) Inventor: Tadao Endo, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/961,082

(22) Filed: Oct. 12, 2004

(65) Prior Publication Data

US 2005/0078785 A1    Apr. 14, 2005

(30) Foreign Application Priority Data

Oct. 14, 2003   (JP) ............................. 2003-354158
Jun. 9, 2004    (JP) ............................. 2004-171226

(51) Int. Cl.
*A61B 6/02* (2006.01)

(52) U.S. Cl. ............................. 378/22; 378/25; 378/26

(58) Field of Classification Search ................ 378/21, 378/22, 25, 26
See application file for complete search history.

(56) References Cited

U.S. PATENT DOCUMENTS

| | | | | |
|---|---|---|---|---|
| 3,626,932 A * | 12/1971 | Becker | ......................... | 378/95 |
| 4,387,722 A * | 6/1983 | Kearns | ......................... | 378/95 |
| 4,903,204 A * | 2/1990 | Dobbins, III | .................. | 378/4 |
| 5,526,442 A * | 6/1996 | Baba et al. | .................. | 382/132 |
| 5,573,012 A * | 11/1996 | McEwan | ..................... | 600/428 |
| 5,877,501 A * | 3/1999 | Ivan et al. | .................. | 378/98.8 |
| 6,075,256 A | 6/2000 | Kaifu et al. | ................... | 257/53 |
| 6,324,249 B1 * | 11/2001 | Fazzio | .......................... | 378/22 |
| 6,611,575 B1 * | 8/2003 | Alyassin et al. | ............... | 378/22 |
| 6,643,536 B2 * | 11/2003 | Nicolas et al. | ............. | 600/428 |
| 6,748,046 B2 * | 6/2004 | Thayer | ......................... | 378/22 |
| 6,904,121 B2 * | 6/2005 | Claus et al. | .................. | 378/21 |
| 6,970,531 B2 * | 11/2005 | Eberhard et al. | ............. | 378/21 |
| 2003/0190010 A1 * | 10/2003 | Tsujii | ......................... | 378/23 |

FOREIGN PATENT DOCUMENTS

JP        8-116044        5/1996

* cited by examiner

*Primary Examiner*—Chih-Cheng G Kao
(74) *Attorney, Agent, or Firm*—Fitzpatrick, Cella, Harper & Scinto

(57) ABSTRACT

To provide a radiation image pick-up device capable of obtaining a plurality of tomography images through single-time image pick-up, a radiation image pick-up method and a program.

When a position controller moves an X-ray source to an optional tomography plane in an object to be detected in parallel and the X-ray source is present at geometric focuses set at equal interval, X rays are pulsatively generated by the X-ray source and detection of X rays by a radiation detector is performed by the total of n times. Moreover, a position controller moves the radiation detector in accordance with the movement of the X-ray source.

19 Claims, 15 Drawing Sheets

FIG. 8

| POINTS IN TOMOGRAPHY PLANE | ... | A20 | A21 | A22 | A23 | A24 | A25 | A26 | A27 | A28 | A29 | A30 | A31 | A32 | A33 | A34 | A35 | A36 | A37 | A38 | A39 | A40 | A41 | A42 | A43 | A44 | A45 | A46 | A47 | A48 | ... |
|---|---|---|---|---|---|---|---|---|---|---|---|---|---|---|---|---|---|---|---|---|---|---|---|---|---|---|---|---|---|---|---|
| F1 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F2 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F3 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F4 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F5 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F6 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F7 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F8 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F9 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F10 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| TOTAL F1+...+F10 | ... | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | ... |

POSITIONS OF X-ray SOURCE

FIG. 10

| POINTS IN TOMOGRAPHY PLANE | ... | B10 | B11 | B12 | B13 | B14 | B15 | B16 | B17 | B18 | B19 | B20 | B21 | B22 | B23 | B24 | B25 | B26 | B27 | B28 | B29 | B30 | B31 | B32 | B33 | B34 | B35 | B36 | B37 | B38 | ... |
|---|---|---|---|---|---|---|---|---|---|---|---|---|---|---|---|---|---|---|---|---|---|---|---|---|---|---|---|---|---|---|---|
| F1 | ... | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | a50 | a51 | ... |
| F2 | ... | a21 | a22 | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | a48 | a49 | ... |
| F3 | ... | a19 | a20 | a21 | a22 | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | a46 | a47 | ... |
| F4 | ... | a17 | a18 | a19 | a20 | a21 | a22 | a23 | a24 | a25 | a26 | a27 | a28 | a29 | a30 | a31 | a32 | a33 | a34 | a35 | a36 | a37 | a38 | a39 | a40 | a41 | a42 | a43 | a44 | a45 | ... |
| F5 | ... | a15 | a16 | a17 | a18 | a19 | a20 | a21 | a22 | a23 | a24 | a25 | a26 | a27 | a28 | a29 | a30 | a31 | a32 | a33 | a34 | a35 | a36 | a37 | a38 | a39 | a40 | a41 | a42 | a43 | ... |
| F6 | ... | a13 | a14 | a15 | a16 | a17 | a18 | a19 | a20 | a21 | a22 | a23 | a24 | a25 | a26 | a27 | a28 | a29 | a30 | a31 | a32 | a33 | a34 | a35 | a36 | a37 | a38 | a39 | a40 | a41 | ... |
| F7 | ... | a11 | a12 | a13 | a14 | a15 | a16 | a17 | a18 | a19 | a20 | a21 | a22 | a23 | a24 | a25 | a26 | a27 | a28 | a29 | a30 | a31 | a32 | a33 | a34 | a35 | a36 | a37 | a38 | a39 | ... |
| F8 | ... | a9 | a10 | a11 | a12 | a13 | a14 | a15 | a16 | a17 | a18 | a19 | a20 | a21 | a22 | a23 | a24 | a25 | a26 | a27 | a28 | a29 | a30 | a31 | a32 | a33 | a34 | a35 | a36 | a37 | ... |
| F9 | ... | a7 | a8 | a9 | a10 | a11 | a12 | a13 | a14 | a15 | a16 | a17 | a18 | a19 | a20 | a21 | a22 | a23 | a24 | a25 | a26 | a27 | a28 | a29 | a30 | a31 | a32 | a33 | a34 | a35 | ... |
| F10 | ... | a5 | a6 | a7 | a8 | a9 | a10 | a11 | a12 | a13 | a14 | a15 | a16 | a17 | a18 | a19 | a20 | a21 | a22 | a23 | a24 | a25 | a26 | a27 | a28 | a29 | a30 | a31 | a32 | a33 | ... |
| TOTAL F1+...+F10 | | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | Σ | |

POSITIONS OF X-ray SOURCE

RADIATION IMAGE PICK-UP DEVICE, RADIATION IMAGE PICK-UP METHOD AND PROGRAM

BACKGROUND OF THE INVENTION

1. Field of the Invention

The present invention relates to a radiation detection system used for a diagnosis in a hospital, a radiation image pick-up device preferably used for an industrial non-destructive inspection, a radiation image pick-up method and a program.

2. Related Background Art

At present, a film system for irradiating a patient with X-rays and exposing its transmitted X-ray image to a film is a main stream of an X-ray still image photographing system in medical treatment. A film is widely spread because it has a function for displaying and recording information, a large area and a high gradation characteristic and is lightweight and easily handled.

There is a tomography photographing method as one of photographing methods using a film. FIG. 15 is a schematic view showing a conventional tomography photographing method using a film. A point F denotes the position of the focus of an X-ray generation source. The X ray from the point F passing through a point O in an objects to be detected (patient) is irradiated to a point S on a film face. That is, the points F, O and S are on a straight line. Then, the points F, O and S are exposed to the film while keeping the points F, O and S on the straight line and moving the X-ray source and the film in parallel with the tomography plane to be photographed. In this case, the X-ray source and film are moved in directions opposite to each other. By performing the above photographing, the tomography plane parallel with the film including the point O is photographed to the tomography plane. This method is generally referred to as a tomography photographing method. In the case of the example shown in FIG. 15, an X-ray tomogram of a tomography plane A including the point O, that is, the tomography plane A for dividing the interval between the X ray and the film at D:d.

In this case, a mechanism from which the X-ray tomogram of the tomography plane A is obtained is described. In the case of the example shown in FIG. 15, a relation of $L_{F_1F_2}/L_{S_1S_2}=D/d$ is effected between the length $L_{F_1F_2}$ of a segment $F_1F_2$ and the length $L_{S_1S_2}$ of a segment $S_1S_2$ and a relation of $L_{F_1F_2}/L_{T_1T_2}=D/d$ is effected between $L_{F_1F_2}$ and the length $L_{T_1T_2}$ of a segment $T_1T_2$. Points $S_1$ and $S_2$ are projection points of the point O from points $F_1$ and $F_2$. Points $T_1$ and $T_2$ are projection points of the point O' from points $F_1$ and $F_2$. Moreover, a relation of $L_{S_1S_2}=LT_1T_2$ is also effected. That is, projection images of the points O and O' are uniquely reflected on the same film face. That is, it is possible to photograph a tomography image connecting the point O with the point O' parallel with the film.

In the case of a point Z separate from the tomography plane A by a distance h to the X-ray source side, the projected image of the point Z moves from a point $U_1$ up to a point $U_2$ in accordance with the movement of the X-ray source. In this case, a relation of $L_{F_1F_2}/L_{U_1U_2}=(D-h)/(d+h)$ is effected between $L_{S_1S_2}$ and the length $L_{U_1U_2}$ of a segment $U_1U_2$ but $L_{F_1F_2}$ does not become equal to $L_{U_1U_2}$ ($L_{F_1F_2}<L_{F_1F_2}$). As a result, the projection image of the point Z is not reflected on the film as a point but it is projected as the linear image of a length ($L_{F_1F_2}-L_{F_1F_2}$). Therefore, the image of an object to be detected (patient) present out of the tomography plane parallel with the film face including the points O and O' like the point Z becomes a linearly fuzzy image but it is not reflected on the film. This is the principle of the tomography photographing method. FIG. 15 shows a tomography plane for dividing an X-ray source and a film into D:d in an objects to be detected (patient). However, it is possible to obtain an optional tomography image by previously selecting a positional relation between an X-ray source, patient and film.

Moreover, a request for digitization of an X-ray image has been recently raised in hospitals. For example, instead of a film an X-ray image pick-up device is started to be used in which X-ray detection devices (solid image pick-up devices) for respectively converting an X-ray dose into an electrical signal are arranged like a two-dimensional array. According to this X-ray image pick-up device, it is possible to instantaneously transmit information to a distant place because an X-ray image can be replaced to digital information. Therefore, for example, it is possible to receive an advanced diagnosis equal to that of a university hospital at an urban center even in a local area. Moreover, by avoiding use of a film, there is an advantage that it is possible to omit a film storing space in a hospital. Then, by using a superior image processing technique in future, a method is expected which automatically diagnoses a patient by using a computer not through a radiation doctor.

In recent years, a radiation image pick-up device capable of photographing a static image is practically used by using the fabrication techniques of an amorphous silicon thin-film semiconductor for a solid image pick-up device. Moreover, change to a large area exceeding 40-cm square covering the region of the chest of a human body is realized.

Furthermore, because the fabrication process is comparatively easy, it is expected to provide an inexpensive detector in future. Furthermore, because it is possible to fabricate amorphous silicon on a thin glass of 1 mm or less, there is an advantage that it is possible to fabricate the detector by greatly deceasing the detector in thickness and weight. Japanese Patent Application Laid-Open No. 8-116044 discloses a radiation image pick-up device using the above amorphous silicon thin-film semiconductor.

However, in the case of a tomography photographing method using a film, though it is possible to optionally decide a tomography plane to be obtained by previously selecting a positional relation between an X-ray source, film and object to be detected (patient), the number of tomograms obtained through one-time photographing is only one. That is, to obtain other tomography plane, it is necessary to perform photographing once more. Moreover, when a desired tomography image is not obtained, there is a case in which retry of photographing is inevitably selected again. This represents that the dosage of exposure to radiation increases for a patient and this is not preferable. Furthermore, the exposure time to a film generally requires several seconds in the case of the tomography photographing method. Therefore, a tomography image around the heart of the patient frequently becomes unclear in a chest tomography image due to the movement of the heat in an exposure period or the movement of breathing of the patient and it is difficult to obtain a preferably tomogram. Moreover, in the case of a method using a film not applied only to the tomography photographing method, many problems are left on management and operation in a hospital by including a problem on a film storage space and a problem that a lot of time is required to search a necessary patient film out of a great number of films in a hospital.

Furthermore, as described above, an X-ray image pick-up device provided with a solid image pick-up element is also developed. However, it is not changed that the number of tomograms obtained through one-time photographing is only one similarly to the case of using a film.

SUMMARY OF THE INVENTION

It is an object of the present invention to provide a radiation image pick-up device for obtaining tomography images in one-time photographing, a radiation iimage pick-up method and a program.

The present invention thinks of various modes of the invention as a result of earnestly repeating study in order to solve the above problem.

A radiation image pick-up device of the present invention is constituted by radiation generation means, radiation detection means in which a plurality of radiation detection elements for respectively converting radiation from the radiation generation means into an electrical signal are arranged like a matrix to detect radiation, read means for reading an electrical signal from the radiation detection means, storage means for storing the electrical signal read by the read means and signal processing means for processing the electrical signal stored in the storage means are included and an object to be detected is set between the radiation generating means and the radiation detection means, the radiation generation means and the radiation detection means move, so that an intersection point between a straight line connecting a point at which an optional radiation detection element selected from the radiation detection elements is located when the radiation detection means detects radiation with a point at which the radiation generation means is located and one plane set in the object to be detected remains substantially of a fixed point and the read means reads electrical signals generated by the radiation detection elements every frame over a plurality of frames.

A first radiation image pick-up method of the present invention is a radiation image pick-up method using a radiation image pick-up device which has radiation generation means, radiation detection means constituted by a plurality of radiation detection elements for respectively converting radiation from the radiation generation means into electrical signal arranged in a matrix to detect radiation and read means for reading an electrical signal from the radiation detection means and in which an object to be detected is set between the radiation generation means and the radiation detection means and the radiation generation means and the radiation detection means are moved, so that an intersection point between a straight line connecting a point at which an optional radiation detection element selected out of the radiation detection elements is located when the radiation detection means detects radiation with a point at which the radiation generation means is located and one plane set in the object to be detected remains substantially of a fixed point and electrical signals generated by the radiation detection elements are read every frame over a plurality of frames.

A second radiation image pick-up method of the present invention is a radiation image pick-up method which has a step of irradiating an object to be detected with radiation from radiation generation means and detecting the radiation passing through the object to be detected and in which the radiation detection means is constituted by a plurality of radiation detection elements for respectively converting the radiation from the radiation generation means into an electrical signal arranged in a matrix, the radiation generation means and the radiation detection means are moved, so that an intersection point between a straight line connecting a point at which an optional radiation detection element selected out of the radiation detection elements is located when the radiation detection means detects radiation with a point at which the radiation generation means is located and one plane set in the object to be detected remains substantially of a fixed point and electrical signals generated by the radiation detection elements are read every frame over a plurality of frames.

A first program of the present invention is a program for making a computer control a radiation image pick-up device which has radiation generation means, radiation detection means constituted by a plurality of radiation detection elements for respectively converting radiation from the radiation generation means into an electrical signal arranged in a matrix to detect radiation, read means for reading an electrical signal from the radiation detection means, storage means for storing an electrical signal read by the read means and signal processing means for processing the electrical signal stored in the storage means and in which an object to be detected is set between the radiation generation means and the radiation detection means and for making the computer execute a step of moving the radiation generation means and the radiation detection means, so that an intersection point between a straight line connecting a point at which an optional radiation detection element selected out of a plurality of radiation detection elements is located when the radiation detection means detects radiation with a point at which the radiation generation means is located and one plane set in the object to be detected remains substantially of a fixed point and a step of reading electrical signals generated by the radiation detection elements every frame over a plurality of frames.

A second program of the present invention is a program for making a computer execute a step of irradiating an object to be detected with radiation from radiation generation means and detecting the radiation passing through the object to be detected by using radiation detection means which is constituted by a plurality of radiation detection elements for respectively converting the radiation from the radiation generation means into an electrical signal arranged in a matrix and for making the computer execute a step of moving the radiation generation means and the radiation detection means, so that an intersection point between a straight line connecting a point at which an optional radiation detection element selected out of the radiation detection elements is located when the radiation detection means detects radiation with a point at which the radiation generation means is located and one plane set in the objects to be detected remains substantially of a fixed point in order to apply and detect the radiation and a step of reading electrical signals generated by the radiation detection elements every frame over a plurality of frames.

According to the present invention, it is possible to properly combine the information obtained every frame in order to read an electrical signal generated by a radiation detection element every frame. By properly adjusting the combination, it is possible to obtain a plurality of tomography images through one-time photographing. Therefore, because a desired tomography image is easily obtained through single-time photographing, the frequency for redoing image pick-up is decreased. As a result, it is possible to prevent increased dosage of exposure to radiation to a patient which is an object to be detected from increasing. Moreover, when synchronizing the beat of the heart of and the movement of lungs due to breathing of a patient with X-ray generation timing, it is possible to obtain a clear preferably tomogram as a tomography image around the heart. Furthermore, because the present invention does not require a film, problems of a film storage and a space in a hospital are solved and the search time for searching a desired tomogram is also decreased. Therefore, many effects can be expected in the management and operation of the hospital.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 8 is an illustration showing processings by the signal processing circuit 104 when obtaining the tomography image of a tomography plane A;

FIG. 10 is an illustration showing processings by the signal processing circuit 104 when obtaining a tomography image of the tomography plane B;

DESCRIPTION OF THE PREFERRED EMBODIMENTS

Figure 1:
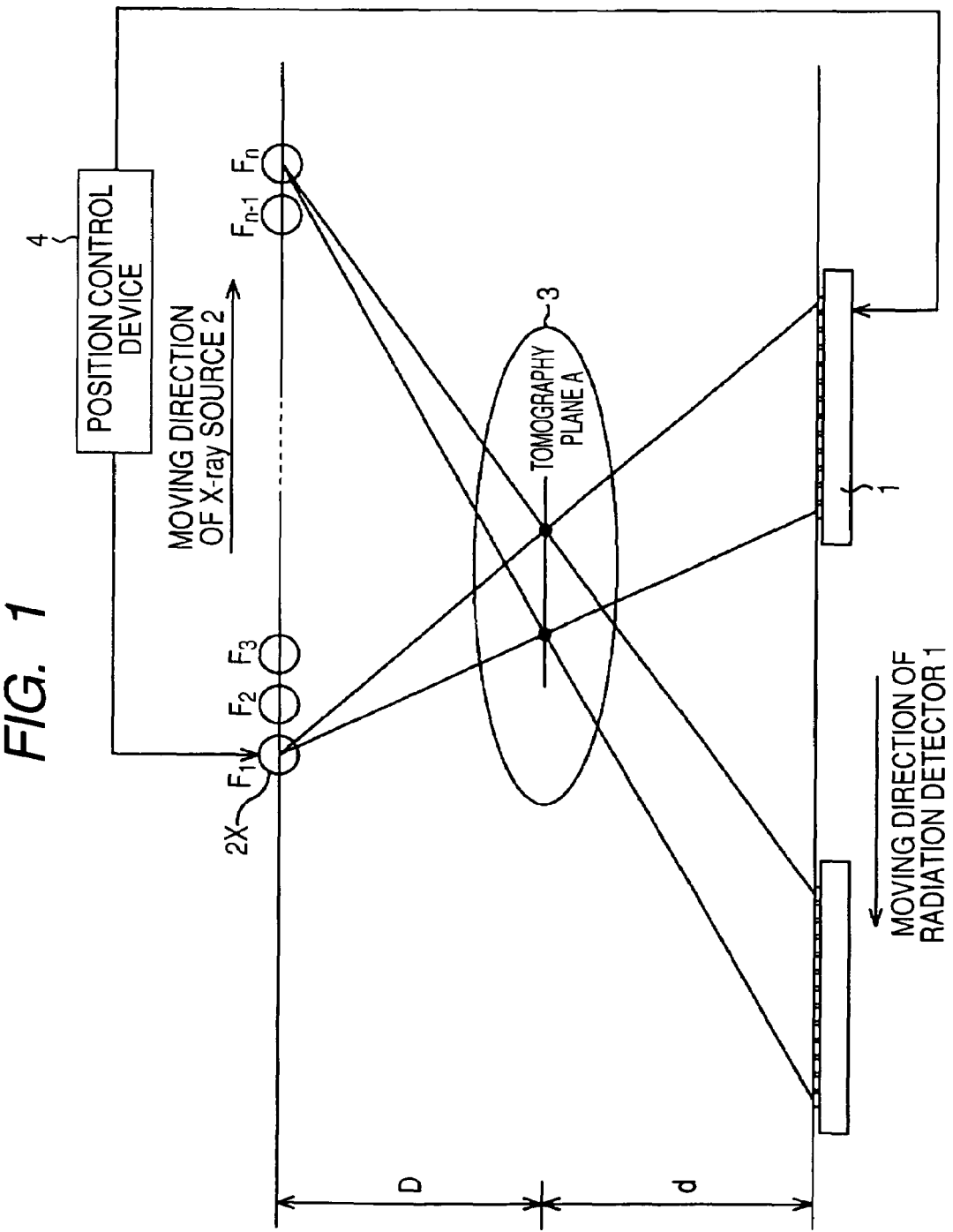
FIG. 1 is a schematic view showing a configuration of an X-ray image pick-up device of an embodiment of the present invention.

Embodiments of the present invention are specifically described below by referring to the accompanying drawings. FIG. 1 is a schematic view showing a configuration of an X-ray image pick-up device (radiation image pick-up device) of an embodiment of the present invention.

In the case of this embodiment, an X-ray source 2 (shown in the drawings as 2x) is set above an object to be detected (patient) 3 and a radiation detector 1 is set under the object to be detected 3. The radiation detector 1 is provided with a plurality of X-ray detection elements (pixels) for converting X rays passing through the object to be detected 3 irradiated from the X-ray source 2 into electrical signals. FIG. 1 shows 13 X-ray detection elements arranged in one direction.

Moreover, this embodiment is provided with a position controller 4 for controlling positions of the radiation detector 1 and X-ray source 2. In the case of this embodiment, the positon controller 4 moves the X-ray source 2 to an optional tomography plane A in the object to be detected 3 in parallel. When the X-ray source 2 is present at geometric focuses $F_1$ to $F_n$ set at equal intervals from each other, an X ray is pulsatively generated by the X-ray source 2 and detection of an X ray by the radiation detector 1 is performed up to the total of n times. That is, one-time image pick-up is performed in accordance with detection for n frames. That is, one-time image pick-up is performed through detection for n frames. Moreover, the position controller 4 moves the radiation detector 1 in accordance with the movement of the X-ray source 2.

In the case of a conventional tomography photographing method using a film, X rays are multiple-exposed to the film for several seconds. However, in the case of this embodiment, X rays are applied each time at positions of the points $F_1$ to $F_n$ instead of exposing X rays to the radiation detector 1 for a long time only once and the image information obtained through that is read each time every frame.

Figure 2:
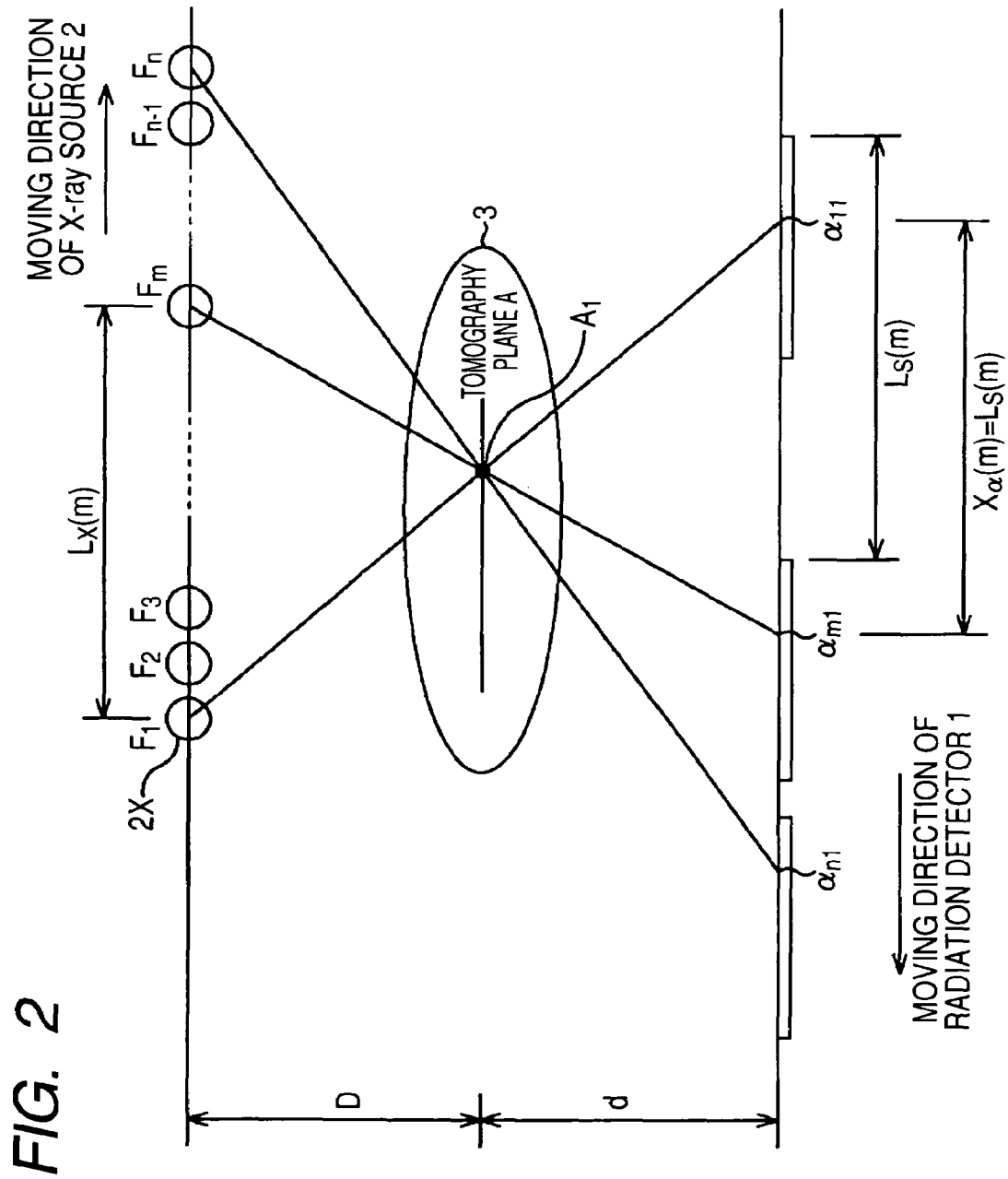
FIG. 2 is a schematic view showing a method of position control by a positon controller 4.

FIG. 2 is a schematic view showing a position control method by the position controller 4. The position controller 4 moves the radiation detector 1 in the direction opposite to the X-ray source 2 so that the position of α point a on the radiation detection 1 at which transmitted X rays passing through an optional point $A_1$ in the tomography plane A arrive (point on an extension line of a segment connecting a point at which X-ray source is located with the point $A_1$) becomes constant. That is, the position controller 4 moves the radiation detector 1 and X-ray source 2 so that when an origin is set on the radiation detector 1, all coordinates on the radiation detector 1 of a point $α_{m1}$ which is irradiated when the X-ray source 2 is present on a point $F_m$ (m is a natural number of n or less) and at which the transmitted X rays passing through the point $A_1$ arrives coincide with each other.

In this case, when assuming the moving distance between m frames (for example, distance between the points $F_1$ and $F_m$) of the X-ray source 2 by the position controller 4 as $L_x(m)$, the moving distance $L_S(m)$ of the radiation detector 1 between m frames corresponding to $L_x(m)$ is shown by Numerical Formula 1. However, D denotes the distance between the tomography plane A and the face on which the radiation detector 1 moves and d denotes the distance between the tomography plane A and the face on which the radiation detection 1 moves.

$$L_S(m) = \frac{d}{D} \times L_X(m) \quad \text{(Numerical Formula 1)}$$

Moreover, because the coordinates of the point $α_{m1}$ on the radiation detector 1 are not changed, the moving distance $xα$ (m) of the point $α_{m1}$ (for example, distance between points $α_{11}$ an $α_{m1}$) between m frames is also $L_S$.

Figure 3:
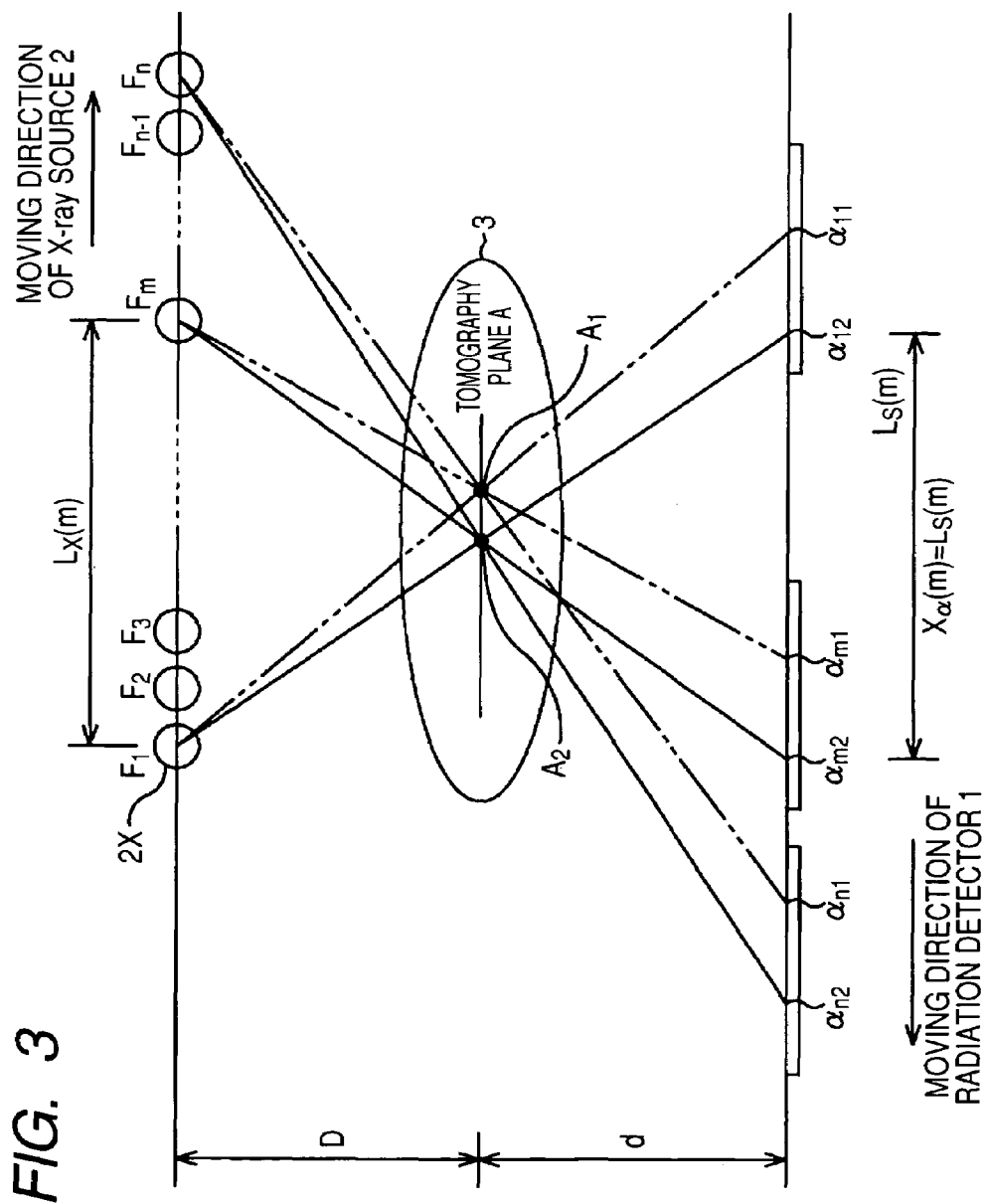
FIG. 3 is a schematic view showing a relation between position control by the position controller 4 and a projection shadow of a point in the tomography plane A.

When the above position control is performed, the position of a point on the radiation detector 1 to which X-rays passing through another optional point in the tomography plane A are applied is not changed as shown in FIG. 3. That is, all coordinates on the radiation detector 1 of a point $\alpha_{m2}$ which is irradiated from the X-ray source 2 on a point $F_m$ and at which X rays passing through an optional point $A_2$ arrives coincide with each other and the moving distance of the point $\alpha_{m2}$ between m frames is also $L_S$.

In other words, the X-ray source 2 and radiation detector 1 move in accordance with the control using the position controller 4 so that the intersection $A_2$ between a straight line connecting the point $\alpha_{m2}$ at which an optional radiation detection element (for example, X-ray detection element at the point $\alpha_{m2}$) is located when the radiation detector 1 (radiation detection means) detects X rays (radiation) and the point $F_m$ at which the X-ray source 2 (radiation generation means) is located and the tomography plane A (one plane) set in the object to be detected 3 substantially becomes a constant point.

Figure 4:
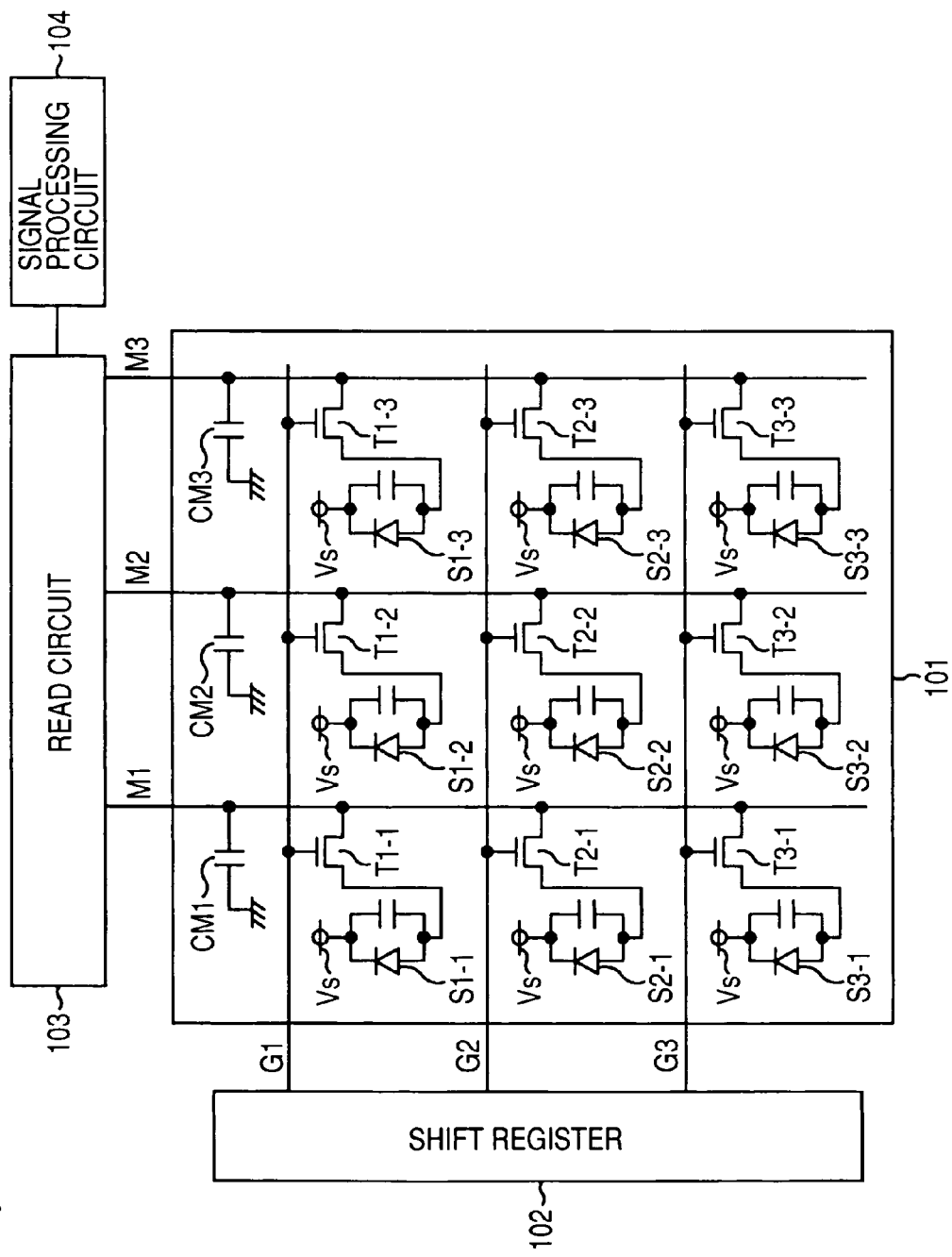
FIG. 4 is a circuit diagram showing a schematic circuit configuration of a radiation detector 1.

Then, the configuration of the radiation detector 1 is described below. FIG. 4 is a circuit diagram showing a schematic circuit configuration of the radiation detector 1. In FIG. 4, x-ray detection elements (photoelectric conversion elements) for 3×3 pixel are illustrated for convenience' sake.

In the case of the radiation detector 1, photoelectric conversion elements S1-1 to S3-3 are arranged on a photoelectric conversion substrate 101 like a matrix and switching elements (TFT) T1-1 to T3-3 are set every photoelectric conversion elements S1-1 to S3-3. Moreover, gate wirings G1 to G3 to which signals for turning on/off the switching elements T1-1 to T3-3 are transmitted and signal wirings M1 to M3 to which electrical signals generated by the photoelectric conversion elements S1-1 to S3-3 are transmitted are set. Furthermore, reading capacitive elements CM1 to CM3 are connected between the signal wirings M1 to M3 and the ground potential. For example, capacities of the reading capacitive elements CM1 to CM3 are equal to the total (for three TFTs) of the inter-electrode capacities (Cgs) between gates and sources of the switching elements (TFTs).

In the case of the photoelectric conversion elements S1-1 to S3-3, photodiodes and capacitive elements are connected in parallel and an inverse-directional bias is applied through a bias wirings Vs. That is, the cathode electrode of a photodiode is biased to be positive. Moreover, electric charges photoelectric-converted by the photodiode are accumulated in capacitive elements. The bias wiring Vs is a wiring common between photoelectric conversion elements. A radiation detection circuit (photoelectric conversion circuit) is constituted by these photoelectric conversion elements S1-1 to S3-3, switching elements T1-1 to T3-3, gate wirings G1 to G3, signal wirings M1 to M3 and bias wiring Vs.

The radiation detector 1 is further provided with a shift resister 102 for applying a pulse signal to the gate wirings G1 to G3 and controlling operations of the photoelectric conversion elements S1-1 to S3-3, a reading circuit 103 for amplifying signals output in parallel through the signal wirings M1 to M3, converting the signals into serial signals and outputting them and a signal processing circuit 104 for processing the electrical signals output from the reading circuit 103. Though not illustrated, the signal processing circuit 104 includes an AD converter circuit (ADC) for converting an analog image signal output from the reading circuit 103 into a digital signal and a storage circuit (memory) for storing the digital data output from the ADC.

A film including a material for directly absorbing X rays and converting them into electrical signals is formed on a circuit such as the radiation detection circuit of the radiation detector 1 or a layered product of a photoelectric conversion body for converting visual light into an electrical signal and a film containing a wavelength conversion body (fluorescent material) for absorbing an X ray and converting it into visual light is formed are formed on the circuit. A material for directly absorbing X rays and converting them into electrical signals can use one of lead iodide ($PbI_2$), mercuric iodide ($HgI_2$), selenium (Se) and gallium arsenide (GaAs). Moreover, the photoelectric conversion body can use a photoelectric conversion element using amorphous silicon as the main material. The wavelength conversion body (fluorescent material) can use one of material using gadolinium oxide ($Gd_2O_3$), gadolinium oxysulfide ($Gd_2O_2S$) and cesium iodide (CsI) as the main material. However, FIG. 1 does not show these materials.

Figure 5:
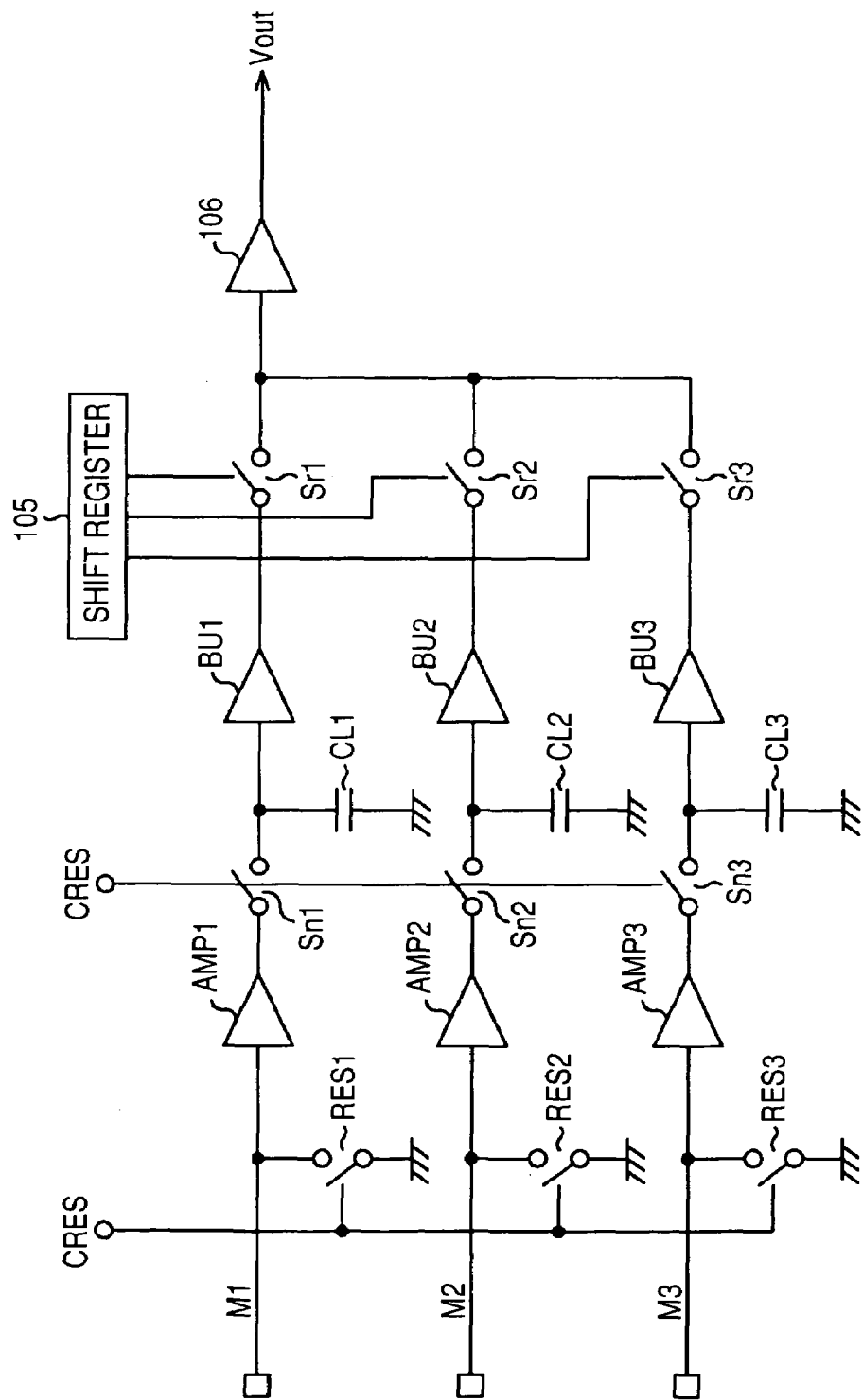
FIG. 5 is a circuit diagram showing a schematic circuit configuration of a reading circuit 103.

Then, the configuration of the reading circuit 103 is described below. FIG. 5 is a circuit diagram showing a schematic circuit configuration of the reading circuit 103. FIG. 5 illustrates portions corresponding to the signal wirings M1 to M3 for convenience' sake.

The reading circuit 103 is provided with switches RES1 to RES3 for resetting potentials of the signal wirings M1 to M3, amplifiers AMP1 to AMP3 for amplifying signals of the signal wirings M1 to M3, sample-holding capacitive elements CL1 to CL3 for temporarily storing signals amplified by the amplifiers AMP1 to AMP3, switches Sn1 to Sn3 for controlling timings to be sample-held by the sample-holding capacitive elements CL1 to CL3, buffer amplifiers BU1 to BU3 and switches Sr1 to Sr3 for series-converting parallel signals. Moreover, the reading circuit 103 is provided with a shift register 105 for supplying pulse signals for series-converting parallel signals to the switches Sr1 to Sr3 and a buffer amplifier 106 for outputting the series-converted signals.

Figure 6:
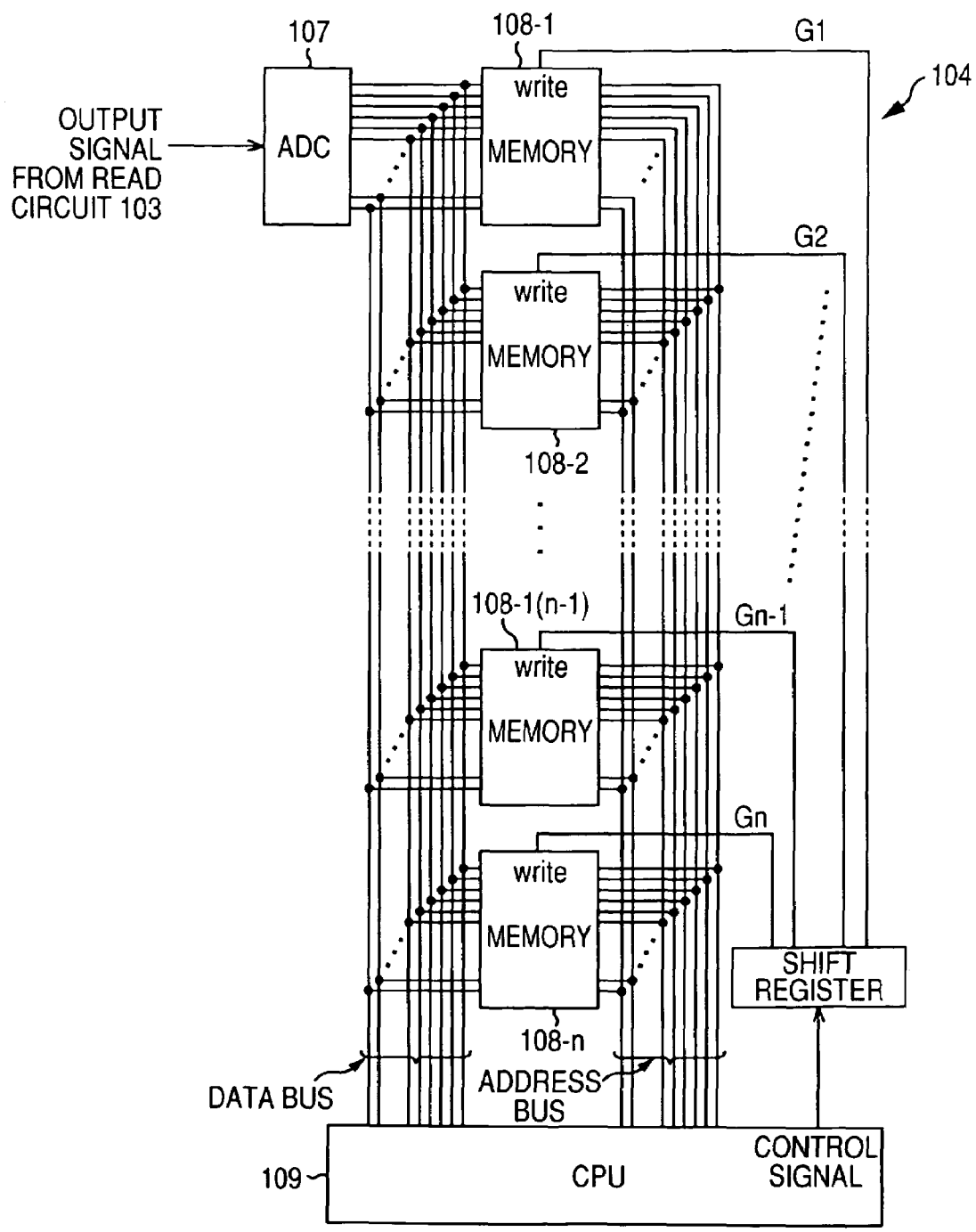
FIG. 6 is a circuit diagram showing a schematic circuit configuration of a signal processing circuit 104.

Then, the configuration of the signal processing circuit 104 is described below. FIG. 6 is a circuit diagram showing a schematic circuit configuration of the signal processing circuit 104.

The signal processing circuit 104 is provided with an AD converter circuit (ADC) 107 for converting analog signals including the X-ray information output from the reading circuit 103 into digital signals. The resolution of the ADC 107 can be adjusted in accordance with a diagnostic purpose. In the case of X-ray-photographing a chest, it is proper to set the resolution to 12 to 14 bits or more. Moreover, the signal processing circuit 104 is provided with n storage circuits (memories) 108-1 to 108-n for storing the data shown by digital signals output from the ADC 107. Signals converted from X rays which are irradiated from the X-ray source 2 at the point $F_1$ and arrive are stored in the storage circuit 108-1 and signals converted from X rays which are irradiated from the X-ray source 2 at the point $F_2$ and arrive are stored in the storage circuit 108-2 and similarly data of X-ray which is irradiated from X-ray source 2 at the point $F_n$ and arrives is stored in the storage circuit 108-n. Data stored in the storage circuits 108-1 to 108-n is processed by a CPU (Central Processing Unit) 109 serving as a computer in the processing circuit 104.

Figure 7:
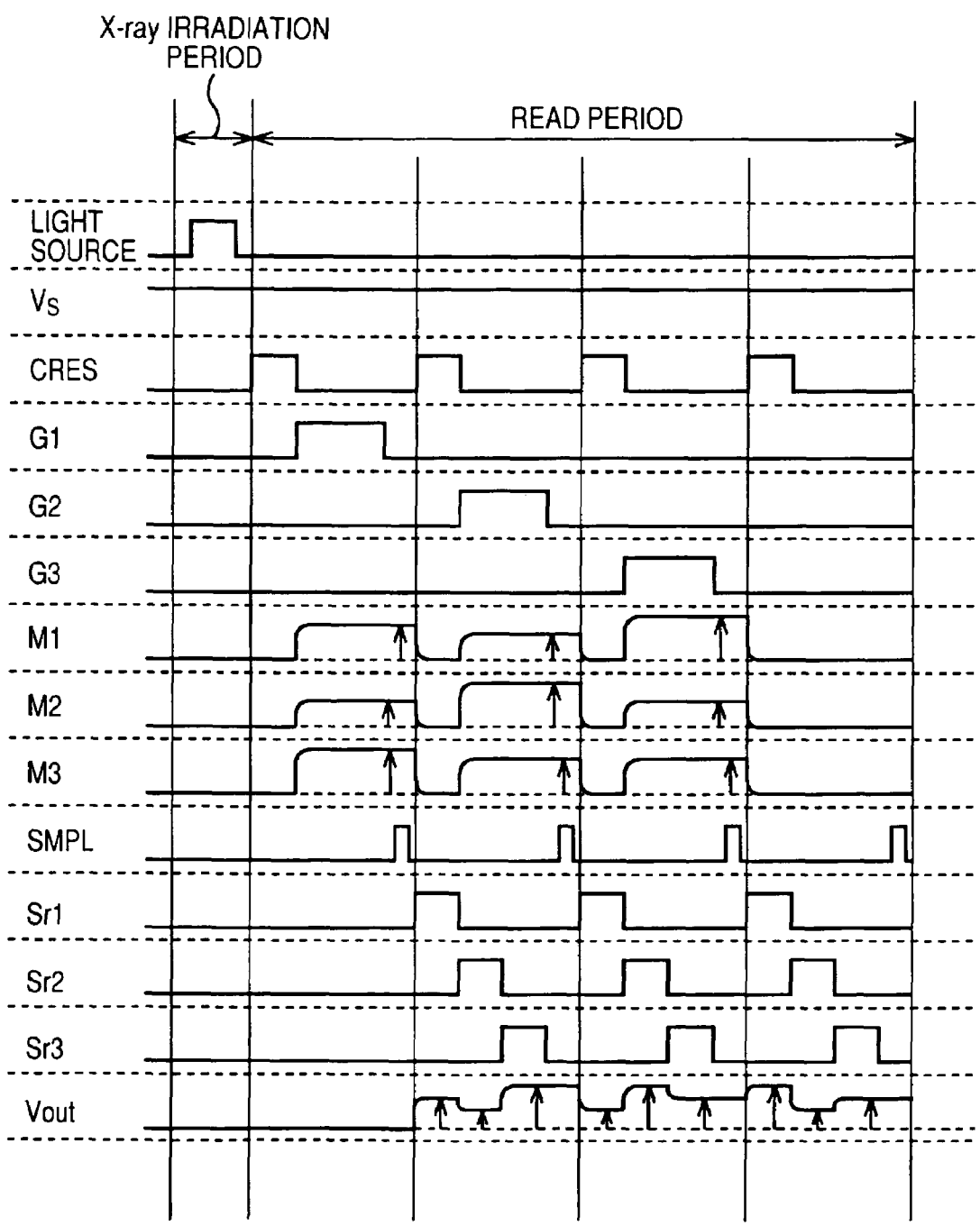
FIG. 7 is a timing chart showing operations for one frame of an X-ray iimage pick-up device.

Then, operations for one frame of an X-ray image pick-up device of this embodiment are described below. FIG. 7 is a timing chart showing operations for one frame of the X-ray image pick-up device. As shown in FIG. 7, one frame is constituted by a photoelectric conversion period (X-ray irradiation period) and a read period.

In the photoelectric conversion period (X-ray irradiation period), the gate wirings G1 to G3 are set to Low and all TFTs are kept at off-state. Under this state, when pulsatively turning on a light source (X ray), X rays passing through the object to be detected 3 are applied to the photoelectric conversion elements S1-1 to s3-3 and signal electric charges corresponding to the quality of X rays are accumulated in capacitive elements. Thereafter, the light source is turned off. However, even after this, signal electric charges are continuously held by the capacitive elements.

The read operation is performed in the read period in order of the first-line photoelectric conversion elements S1-1 to S1-3, second-line photoelectric conversion elements S2-1 to S2-3 and third-line photoelectric conversion elements S3-1 to S3-3.

In the case of read of the first-line photoelectric conversion elements S1-1 to S1-3, a gate pulse is supplied from the shift register 102 to the gate wiring G1 of the switching elements (TFTs) T1-1 to T1-3. Thereby, the switching elements T1-1 to T1-3 are turned on and signal electric charges accumulated in the photoelectric conversion elements S1-1 to S1-3 are transferred to the signal wirings M1 to M3. As described above, because the read capacitive elements CM1 to CM3 are added to the signal wirings M1 to M3, the signal electric charges are transferred to the read capacitive elements CM1 to CM3 through the switching elements T1-1 to T1-3. Moreover, the signal electric charges transferred to the read capacitive elements CM1 to CM3 are amplified by the amplifiers AMP1 to AMP3 in the reading circuit 103.

Moreover, the signal electric charges amplified by the amplifiers AMP1 to AMP3 are transferred to the sample-holding capacitive elements CL1 to CL3 and held by the sample-holding capacitive elements CL1 to CL3 when turning on a SMPL signal and then turning off the SMPL signal. Then, when applying a pulse signal in order of switches Sr1, Sr2 and Sr3 from the shift register 105, the signals held by the sample-holding capacitive elements CL1 to CL3 are amplified by the amplifier 106 in order of the sample-holding capacitive elements CL1, CL2 and CL3 through the buffer amplifiers BU1 to BU3 and then output. In this case, because analog signals output from the buffer amplifiers BU1 to BU3 are output from the amplifier 104, a circuit constituted by the buffer amplifies BU1 to BU3, shift register 105, switches Sr1 to Sr3 and amplifier 106 can be also referred to as an analog multiplexer. Therefore, photoelectric conversion signals for one line generated by the photoelectric conversion elements S1-1, S1-2 and S1-3 can be output in order by the analog multiplexer.

Read operations of the photoelectric conversion elements S2-1 to S2-3 constituting the second line and read operations of the photoelectric conversion elements S3-1 to S3-3 constituting the third line are performed similarly to the case of the first line. When sample-holding signals of the signal wirings M1 to M3 in the sample-holding capacitive elements CL1 to CL3 by using the SMPL signal at the time of read from the first-line photoelectric conversion elements S1-1 to S1-3, it is possible to apply the gate pulse of the gate wiring G2 after resetting potentials of the signal wirings M1 to M3 to the GND potential by using a CRES signal. That is, because superimposition of signals does not occur, it is possible to transfer the signal electric charges of the second-line photoelectric conversion elements S2-1 to S2-3 by using the shift register 102 while series-converting the first-line signals by using the shift register 105. It is possible to output the signal electric charges of the photoelectric conversion elements S1-1 to S3-3 from the first line to third line in accordance with the above operations.

Then, a method for obtaining an X-ray tomogram by using the X-ray image pick-up device of this embodiment is described below. First, n frames are detected in accordance with the above method while moving the radiation detector 1 and X-ray source 2 as shown in FIGS. 2 and 3. As a result, the data at the m-th frame is stored in a storage circuit 108-m.

When a tomography plane to be photographed in the object to be detected 3 is a tomography plane (such as the tomography plane A shown in FIGS. 2 and 3) in which a coordinate of points at which X rays passing through the object to be detected 3 are irradiated on the radiation detector 1 is constituted by the aggregate of constant points, it is only necessary to directly add data values read from the same photoelectric conversion elements (pixels) and once stored in the storage circuit 108-m between ten frames and obtain the sum total of the data values as shown in FIG. 8. That is, as shown in FIG. 8, for example, to obtain the image of a point $A_{30}$, it is only necessary to read the data for a pixel "a33" from storage circuits 108-1 to 108-0 about the first to tenth frames and add these data values and obtain the sum total of the data values. This is because X-ray information on the same point in the tomography plane A is included in the directly added pixel data. Moreover, by obtaining the average value of pixel data values on each point in the tomography plane A to be photographed, it is possible to obtain an X-ray tomogram of the tomography plane A. In FIG. 8, it is assumed that "n=10" is set for convenience'sake, X rays are detected by the radiation detector 1 when the X-ray source 2 is present at the points $F_1$ to $F_{10}$ and one X-ray tomogram is obtained from 10 frames. However, it is not necessary that the value of n is 10. Moreover, "a23" to "a51" in FIG. 8 are numbers added to pixels (photoelectric conversion elements) arranged along the moving direction of the radiation detector 1.

Figure 9:
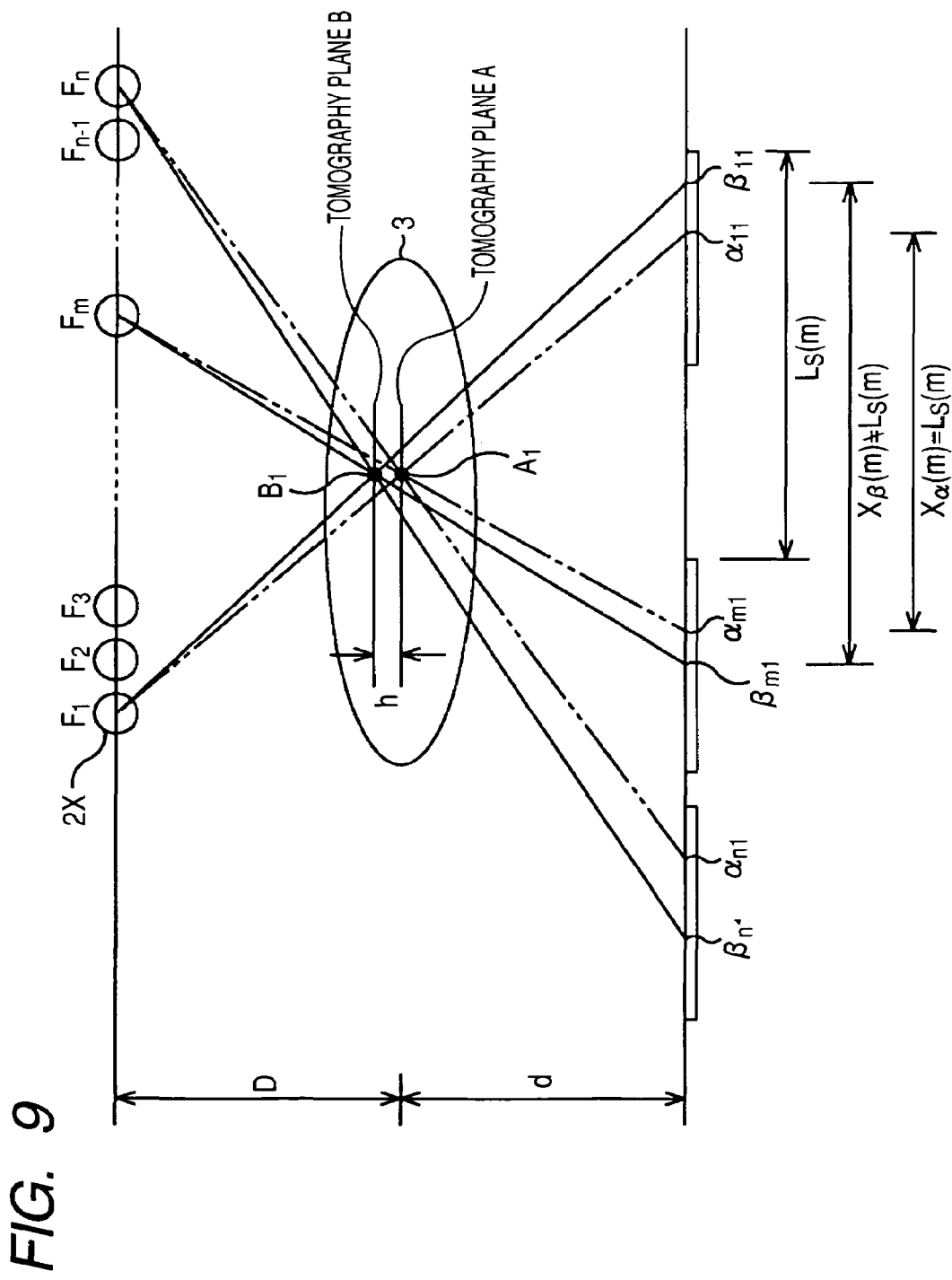
FIG. 9 is a schematic view sowing a method for obtaining an X-ray tomogram of a tomography plane B.

Then, as shown in FIG. 9, a method for obtaining an X-ray tomogram of the tomography plane B at a position separate from the tomography plane A by a distance h to the X-ray source-2 side is described below.

As described above, in the case of this embodiment, the X-ray source 2 moves by $L_x(m)$ and the radiation detector 1 moves by $L_S(m)$ between m frames. Therefore, a moving distance $x\beta(m)$ between m frames of the point $\beta_{m1}$ on the radiation detector 1 at which X rays passing through the point $B_1$ located immediately above the pint $A_1$ in the tomography plane B arrive is shown by Numerical Formula 2.

$$x_\beta(m) = \frac{d+h}{D-h} \times L_X(m) \qquad \text{(Numerical Formula 2)}$$

Therefore, the moving distance $x\beta$ (m) does not coincide with the moving distance $L_S(m)$ of the radiation detector 1. Thereby, the X-ray tomogram of the tomography plane B is not obtained only by directly adding data values read from the same photoelectric conversion elements (pixels) between n frames.

In this case, when noticing the coordinates of the point $\beta_{m1}$ on the radiation detector 1, coordinates of the point $\beta_{m1}$ on the radiation detector 1 are deviated from coordinates at the time of the first frame by a value $Z_x$ (m) shown by Numerical Formula 3 between in frames.

$$Z_X(m) = \qquad \text{(Numerical Formula 3)}$$
$$x_\beta(m) - L_S(m) = \frac{d+h}{D-h} \times L_X(m) - \frac{d}{D} \times L_X(m) =$$
$$\frac{h \times (D+d)}{D \times (D-h)} \times L_X(m)$$

In this case, as described above, because a moving distance $L_x(2)$ between two continuous frames of the X-ray source 2 by the position controller 4 is constant, a displacement value $Z_x(2)$ is also constant. Therefore, the point $\beta_{m1}$ is displaced by a constant value every frame (between two continuous frames)

Therefore, when the displacement value $Z_x(2)$ {$x\beta(2)-L_S(2)$} between two continuous frames corresponds to two pixels (two photoelectric conversion elements), it is only necessary to add read data values between n frames while displacing the data values every two pixels and obtain the sum total of the data values when processing data stored in the storage circuit 108-1 to 108-n. That is, as shown in FIG. 10, to obtain a point $B_{30}$, the data for a pixel "a43" is read from the storage circuit 108-1 for the first frame, the data for a pixel "a41" displaced by two pixels from the pixel "a43" is read from the storage circuit 108-2 for the second frame and the data for a pixel "a39" displaced from the pixel "a41" by two pixels is read from the storage circuit 108-2 for the third frame. Hereafter, while setting a displacement for two pixels, it is only necessary to finally read the data for a pixel "a25" two pixels displaced from a pixel "a27" (read object of ninth frame) from the storage circuit 108-10 for the tenth frame and add these values and obtain the sum total of the values. This is because X-ray information on the same point in the tomography plane B is included in the pixel data displaced every two pixels obtained between the first to tenth frames. Moreover, by obtaining the average value of pixel data values on each point in the tomography plane B to be photographed, it is possible to obtain an X-ray tomogram of the tomography plane B.

Moreover, it is possible to consider a mechanism from which pixel data for points in the tomography plane B is obtained as described below.

Figure 11:
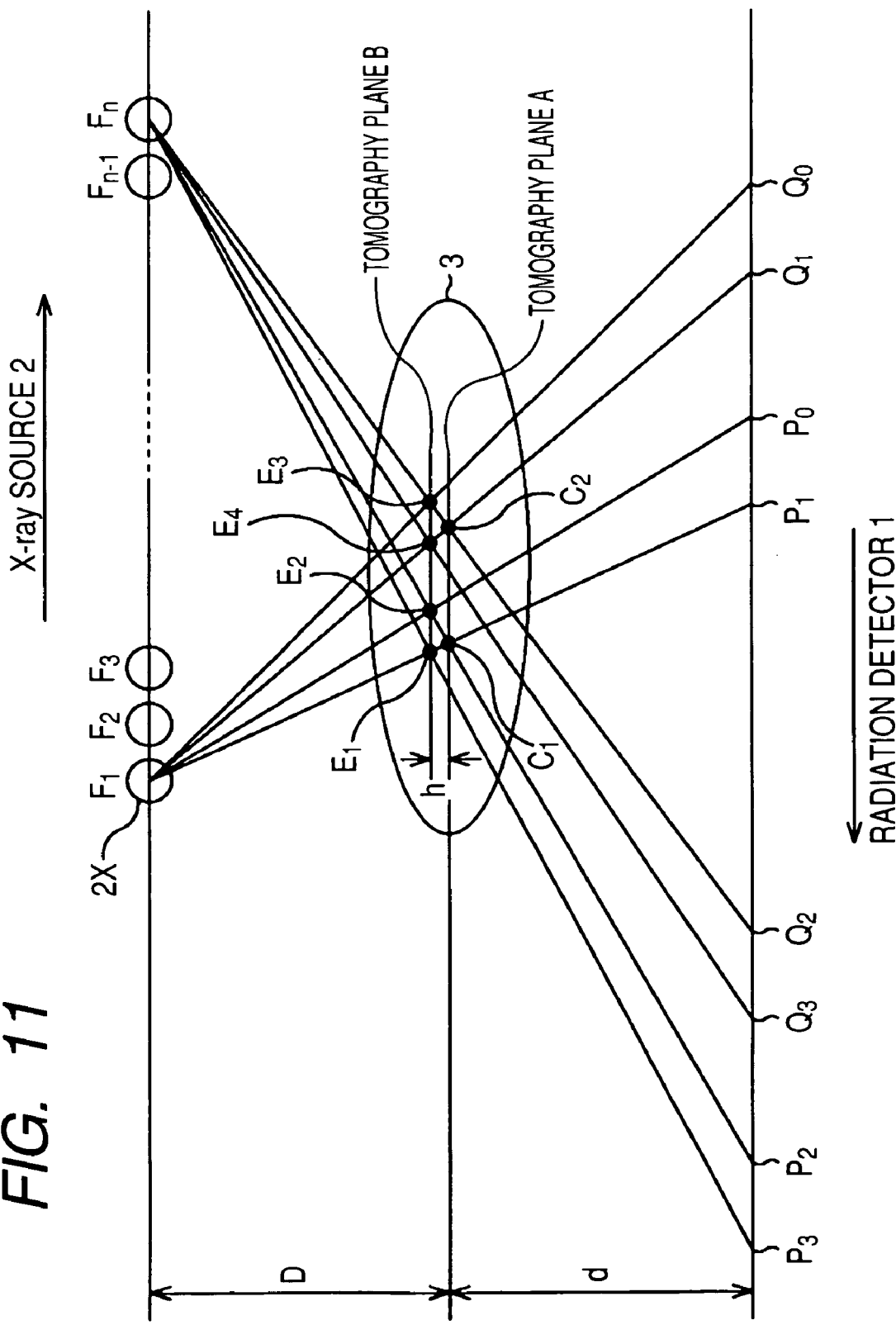
FIG. 11 is a schematic view showing a mechanism from which pixel data for a point in the tomography plane B is obtained.

As shown in FIG. 11, X rays applied to the point $C_1$ in the tomography plane A from the X-ray source 2 present at the point $F_1$ are applied to the point $P_1$ on the radiation detector 1 present on the extension line of the X rays and X rays applied to the point $C_1$ from the X-ray source 2 at the point $F_n$ is applied to the point $P_2$ on the radiation detector 1 present on the extension line of the X-rays. Because the point $C_1$ is a point in the tomography plane A, coordinates of the point $P_2$ on the radiation detector 1 coincide with coordinates of the point $P_1$ on the radiation detector 1. That is, the pixel located at the point $P_2$ is the same as the pixel located at the point $P_1$. Similarly, X rays applied to the point $C_2$ in the tomography plane A from the X-ray source 2 at the point $F_1$ are applied to a point $Q_1$ on the radiation detector 1 present on the extension line of the X rays and X rays applied to the point $C_2$ from the X-ray source 2 at the point $F_n$ is applied to the point $Q_2$ on the radiation detector 1 on the extension line. Because the point $C_2$ is a point in the tomography plane A, coordinates of the point $Q_2$ on the radiation detector 1 coincide with coordinates of the point $Q_1$ on the radiation detector 1 as descried above. Therefore, the equality of Numerical Formula 4 is effected between segments $P_1Q_1$ and $P_2Q_2$.

$$\overline{P_1Q_1} = \overline{P_2Q_2} \qquad \text{(Numerical Formula 4)}$$

Figure 12:
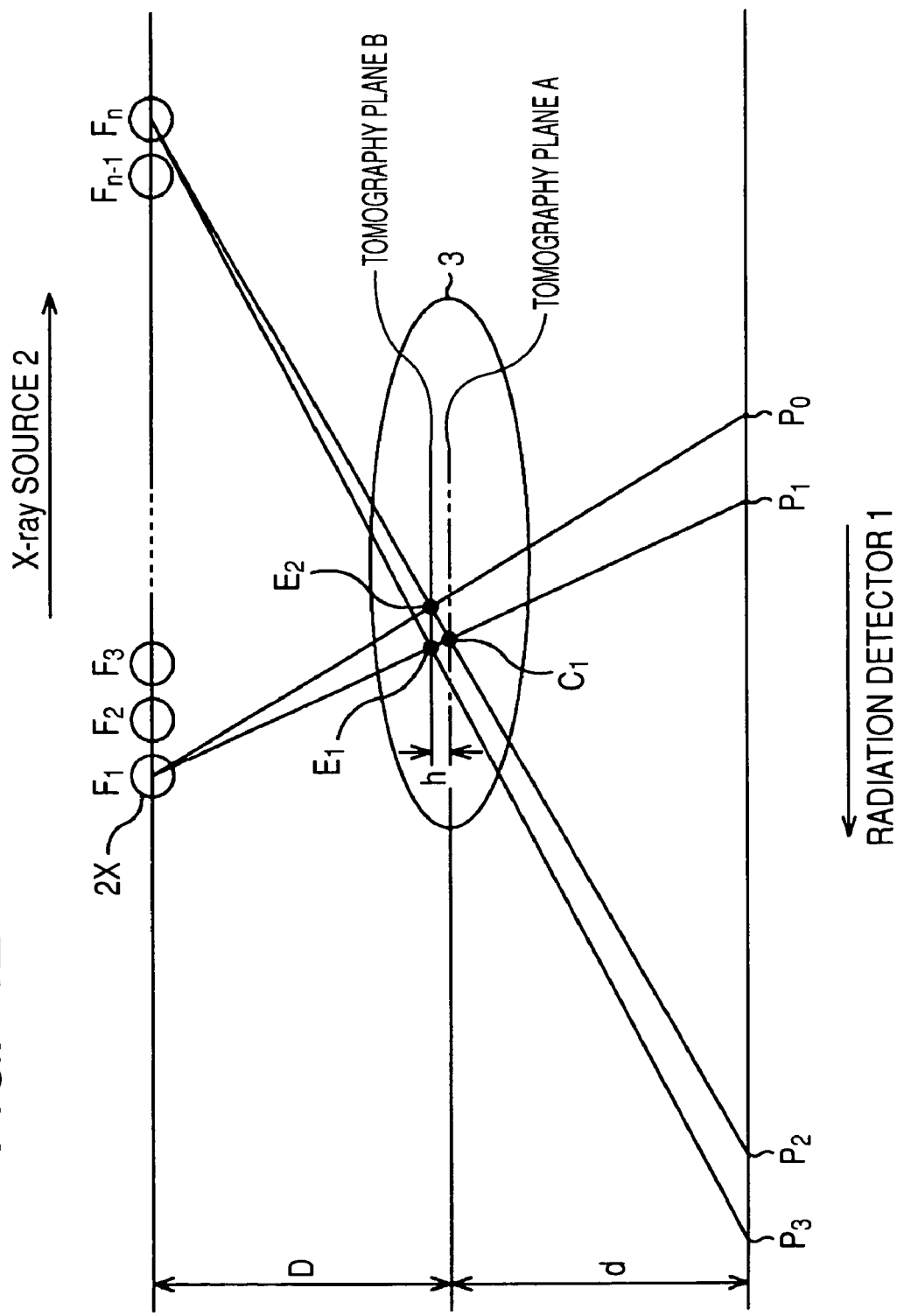
FIG. 12 is a schematic view sowing a relation between points $C_1$, $E_1$ and $E_2$ in an object 3 to be detected and projection shades of these points.

Moreover, as shown in FIG. 12, not only the information on the point $C_1$ but also the information on the point $E_1$ in the tomography plane B are included in the information obtained from X rays (X rays $F_1$->$P_1$) emitted from an X-ray source located at the point $F_1$ and arriving at the point $P_1$. Similarly, the information on the point E1 is included in the information obtained from X rays (X rays $F_n$->$P_3$) emitted from an X-ray source located at the point $F_n$ and arriving at the point $P_3$ through the point $E_1$ in the tomography plane B. However, the point $P_1$ is different from the point $P_3$ in coordinates on the radiation detector 1. That is, the pixel located at the point $P_1$ is different from the pixel located at the point $P_3$. However, as described above, the pixel located at the point $P_1$ is the same as the pixel located at the point $P_2$. Therefore, X rays including the information on the point E1 are applied to a pixel separate from the point $P_2$ by the interval between the points $P_2$ and $P_3$ from the X-ray source 2 on the point $F_n$.

In this case, an analogous relation and the equality of Numerical Formula 5 are effected between triangles $\Delta F_n E_2 E_1$ and $\Delta F_n P_2 P_3$.

$$\frac{\overline{E_2 E_1}}{\overline{P_2 P_3}} = \frac{D-h}{D+d} \qquad \text{(Numerical Formula 5)}$$

Moreover, the point $E_2$ is irradiated from an X-ray source located at the point $F_n$, which is a point in the tomography plane B to be used as a route of X-rays (X rays $F_n$->$P_2$) arriving at the point $P_2$ through the point $C_1$ in the tomography plane A.

Therefore, not only the information on the point $A_3$ but also the information on the point $E_2$ in the tomography plane B are included in the information obtained from X rays (X rays $F_n$->$P_2$) emitted from an X-ray source located at the point $F_n$ and arriving at the point $P_2$. Similarly, the information on the point $E_2$ is included in the information obtained from X rays (X rays $F_1$->$P_0$) emitted from an X-ray source located at the point $F_1$ and arriving at the point $P_0$ through the point $E_2$ in the tomography plane B. However, the point $P_0$ is different from the point $P_2$ in coordinates on the radiation detector 1. That is, the pixel located at the point $P_0$ is different from the pixel located at the point $P_2$. Moreover, as described above, the pixel located at the point $P_1$ is the same as the pixel located at the point $P_2$ as described above. Therefore, X rays including the information on the point $E_2$ are applied to a pixel separate from the point $P_1$ by the interval between the points $P_1$ and $P_0$ from the X-ray source 2 at the point $F_1$.

In this case, an analogous relation and the equality of Numerical Formula 6 are effected between triangles $\Delta F_1 E_2 E_1$ and $\Delta F_1 P_0 P_1$.

$$\frac{\overline{E_2 E_1}}{\overline{P_0 P_1}} = \frac{D-h}{D+d} \qquad \text{(Numerical Formula 6)}$$

Therefore, the equality of Numerical Formula 7 is effected in accordance with Numerical Formulas 5 and 6.

$$\overline{P_2 P_3} = \overline{P_0 P_1} \qquad \text{(Numerical Formula 7)}$$

Figure 13:
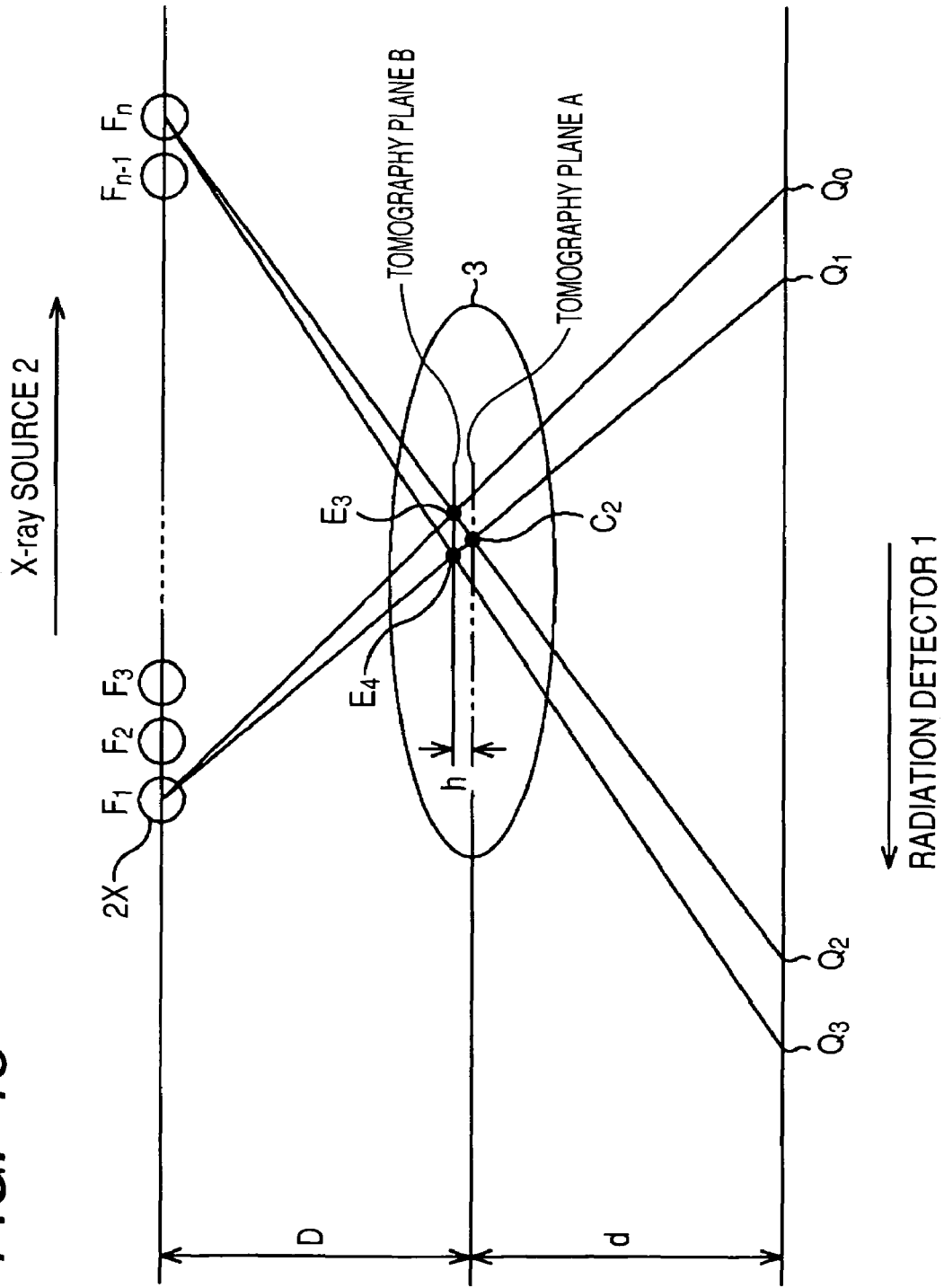
FIG. 13 is a schematic view showing a relation between points $C_2$, $E_3$ and $E_4$ in the object 3 to be detected and projection shades of these points.

Moreover, as shown in FIG. 13, not only the information on the point $C_2$ but also the information on the point $E_3$ in the tomography plane B are included in the information obtained from X rays (X ray $F_n$->$Q_2$) emitted from an X-ray source located at the point $F_n$ and arriving at the point $Q_2$. Similarly, the information on the point $E_3$ is included in the information obtained from X rays (X rays $F_1$->$Q_0$) emitted from an X-ray source located at the point $F_1$ and arriving at the point $Q_0$ through the point $E_3$ in the tomography plane B.

In this case, an analogous relation and the equality of Numerical Formula 8 are effected between triangles $\Delta F_1 E_3 E_4$ and $\Delta F_1 Q_0 Q_1$.

$$\frac{\overline{E_3 E_4}}{\overline{Q_0 Q_1}} = \frac{D-h}{D+d} \quad \text{(Numerical Formula 8)}$$

The point $E_4$ is a point in the tomography plane B to be used as a path by X-rays (X rays $F_1 \rightarrow Q_1$) emitted from an X-ray source located at the point $F_1$ and arriving at the point $Q_1$ through the point $C_2$ in the tomography plane A.

Therefore, not only the information on the point $C_2$ but also the information on the point $E_4$ in the tomography plane B are included in the information obtained from X rays (X rays $F_1 \rightarrow Q_1$) emitted from an X-ray source located at the point $F_1$ and arriving at the point $Q_1$. Similarly, the information on the point $E_4$ is included in the information obtained from X rays (X rays $F_n \rightarrow Q_3$) emitted from an X-ray source located at the point $F_n$ and arriving at the point $Q_3$ through the point $E_4$ in the tomography plane B.

In this case, an analogous relation and the equality of Numerical Formula 9 are effected between triangles $\Delta F_n E_3 E_4$ and $\Delta F_n Q_2 Q_3$.

$$\frac{\overline{E_3 E_4}}{\overline{Q_2 Q_3}} = \frac{D-h}{D+d} \quad \text{(Numerical Formula 9)}$$

Therefore, the equality of Numerical Formula 10 is effected in accordance with Numerical Formulas 8 and 9.

$$\overline{Q_2 Q_3} = \overline{Q_0 Q_1} \quad \text{(Numerical Formula 10)}$$

Moreover, as shown in FIG. 11, an analogous relation and the equality of Numerical Formula 11 are effected between triangles $\Delta F_1 E_2 E_4$ and $\Delta F_1 P_0 Q_1$.

$$\frac{\overline{E_2 E_4}}{\overline{P_0 Q_1}} = \frac{D-h}{D+d} \quad \text{(Numerical Formula 11)}$$

Similarly, an analogous relation and the equality of Numerical Formula 12 are effected between triangles $\Delta F_n E_2 E_4$ and $\Delta F_n P_2 Q_3$.

$$\frac{\overline{E_2 E_4}}{\overline{P_2 Q_3}} = \frac{D-h}{D+d} \quad \text{(Numerical Formula 12)}$$

Therefore, the equality of Numerical Formula 13 is effected in accordance with Numerical Formulas 11 and 12.

$$\overline{P_2 Q_3} = \overline{P_0 Q_1} \quad \text{(Numerical Formula 13)}$$

Moreover, the relation of Numerical Formula 14 is effected in accordance with Numerical Formulas 4, 7, 10 and 13.

$$\overline{Q_0 Q_1} = \overline{P_0 P_1} = \overline{Q_2 Q_3} = \overline{P_2 P_3}$$

According to Numerical Formula 14, in the case of this embodiment, by controlling positions of the radiation detector 1 and X-ray source 2 by the position controller 4, it can be said that all information on points constituting the tomography plane B separate from the tomography plane A to the X-ray source-2 side are projected to photoelectric conversion elements (pixel) separate from each other by equal intervals.

Then, the length of a segment $Q_0 Q_1$ is described which corresponds to the displacement value of photoelectric conversion elements (pixels) when the X-ray source 2 moves from the point $F_1$ to the point $F_n$. First, an analogous relation and the equality of Numerical Formula 15 are effected between triangles $\Delta E_3 F_1 F_n$ and $\Delta E_3 Q_0 Q_2$.

$$\frac{\overline{F_1 F_n}}{\overline{Q_0 Q_2}} = \frac{D-h}{d+h} \quad \text{(Numerical Formula 15)}$$

Therefore, the length of the segment $Q_0 Q_2$ is shown by Numerical Formula 16.

$$\overline{Q_0 Q_2} = \frac{d+h}{D-h} \times \overline{F_1 F_n} \quad \text{(Numerical Formula 16)}$$

Moreover, an analogous relation and the equality of Numerical Formula 17 are effected between triangles $\Delta C_2 F_1 F_n$ and $\Delta C_2 Q_1 Q_2$.

$$\frac{\overline{F_1 F_n}}{\overline{Q_1 Q_2}} = \frac{D}{d} \quad \text{(Numerical Formula 17)}$$

Therefore, the length of the segment $Q_1 Q_2$ is shown by Numerical Formula 18.

$$\overline{Q_1 Q_2} = \frac{d}{D} \times \overline{F_1 F_n} \quad \text{(Numerical Formula 18)}$$

The length of the segment $Q_0 Q_1$ is shown by Numerical Formula 19 in accordance with Numerical Formulas 16 and 18.

$$\overline{Q_0 Q_1} = \overline{Q_0 Q_2} - \overline{Q_1 Q_2} = \frac{d+h}{D-h} \times \overline{F_1 F_n} - \frac{d}{D} \times \overline{F_1 F_n} = \frac{h \times (D+d)}{D \times (D-h)} \times \overline{F_1 F_n} \quad \text{(Numerical Formula 19)}$$

According to Numerical Formula 19, it is possible to specify positions of photoelectric conversion elements (pixels) from which the information on points constituting the tomography plane B are obtained in accordance with four variables such as a distance D between the tomography plane A and a plane on which the X-ray source 2 moves, a distance d between the tomography plane A and a plane on which the radiation detector 1 moves, the distance h between the tomography planes B and A and the length of a segment $F_1 F_n$ showing the total moving distance of the X-ray source 2. In other words, by using the above four variables, it is possible to obtain optional tomography information of a patient, that is, an X-ray tomogram of the patient.

Then, when assuming "n=10", the length of the segment $Q_0 Q_1$ is shown by Numerical Formula 20.

$$\overline{Q_0 Q_1} = \frac{h \times (D+d)}{D \times (D-h)} \times \overline{F_1 F_{10}} \quad \text{(Numerical Formula 20)}$$

In this case, the length of the segment $Q_0Q_1$ corresponds to a displacement value $Z_x(10)$ of a photoelectric conversion element (pixel) when the X-ray source 2 moves from the point $F_1$ to the point $F_n$ and the length of the segment $F_1F_n$ corresponds to $L_x(10)$. Therefore, it is possible to show Numerical Formula 20 as Numerical Formula 21.

$$Z_x(10) = \frac{h \times (D+d)}{D \times (D-h)} \times L_x(10) \qquad \text{(Numerical Formula 21)}$$

Moreover, by generalizing Numerical Formula 21, an expression (Numerical Formula 22) same as Numerical Formula 3 is derived.

$$Z_x(m) = \frac{h \times (D+d)}{D \times (D-h)} \times L_x(m) \qquad \text{(Numerical Formula 22)}$$

Values of "Lx(m)", "D" and "d" in Numerical Formulas 3 and 22 are fixed values decided at start of photographing and "h" can be selected at the time of signal processing in accordance with a tomography plane to be photographed. Therefore, in the case of the above description, a signal processing when a displacement of two pixels occurs between two continuous frames is used. However, according to this embodiment, it is possible to obtain X-ray tomograms of not only the tomography plane B but also an optional tomography plane by changing the value of "h".

In the case of the tomography plane A, an X-ray tomogram can be obtained by directly integrating the tomography plane A without applying pixel displacement as described above. In other words, because h becomes 0 in Numerical Formulas 3 and 22, it is also possible to regard $Z_x(m)=0$.

Moreover, photoelectric conversion elements (pixels) are arranged in a two-dimensional space at equal pitches as shown in FIG. 4. However, $Z_x(m)$ obtained from Numerical Formulas 3 and 22, particularly the value of $Z_x(2)$ may not be integral multiples of a pixel pitch. In this case, it is also allowed to obtain an integer by rounding off after the decimal point of a value obtained by dividing $Z_x(2)$ by a pixel pitch or obtain an integer by moving the value forward or downward. That is, it is enough that read data can be selected from a pixel closest to the pixel specified in accordance with the displacement value $Z_x(2)$ of photoelectric conversion elements (pixels) between two continuous frames.

In the above description, to control positions of the radiation detector 1 and X-ray source 2 by the positon controller 4, the X-ray source 2 is stopped at the points $F_1$, $F_2$, ... and $F_n$ to apply X rays. However, it is not necessary to stop application of X rays but it is allowed to continuously move the X-ray source 2 while continuing application of X rays. Similarly, it is not necessary to stop movement of the radiation detector 1 every detection (read) but it is allowed to perform detection while continuously moving the detector 1. However, when comparing the above case with a case of performing photographing by stopping the detector 1, the quality of a tomography image may be slightly deteriorated when continuously performing photographing.

Moreover, the above description says that one X-ray tomogram is obtained from 10 frames. The image quality of an obtained tomogram is improved as more minutely setting the moving distance $L_x(2)$ and $L_s(2)$ and increasing the number of photographed sheets.

Furthermore, moving directions of the radiation detector 1 and X-ray source 2 are not restricted to one-dimensional direction. It is also allowed to move the radiation detector 1 and X-ray source 2 in the depth direction of the paper of FIG. 1 such as two-dimensional direction. In this case, though a signal processing method slightly becomes complex, it is allowed to perform the signal processing in which the method shown in FIGS. 8 and 10 is applied in two-dimensional direction.

Furthermore, it is not necessary that movements of the radiation detector 1 and X-ray source 2 are linear but it is allowed to curvedly move them. For example, it is allowed to move the radiation detector 1 and X-ray source 2 in a circular orbit, elliptic orbit, or spiral orbit.

Furthermore, it is not necessary to move the radiation detector 1 and X-ray source 2 in parallel with each other but it is allowed to move the radiation detector 1 and X-ray source 2 in a circular arc about an optional point in the object to be detected 3.

Figure 14:
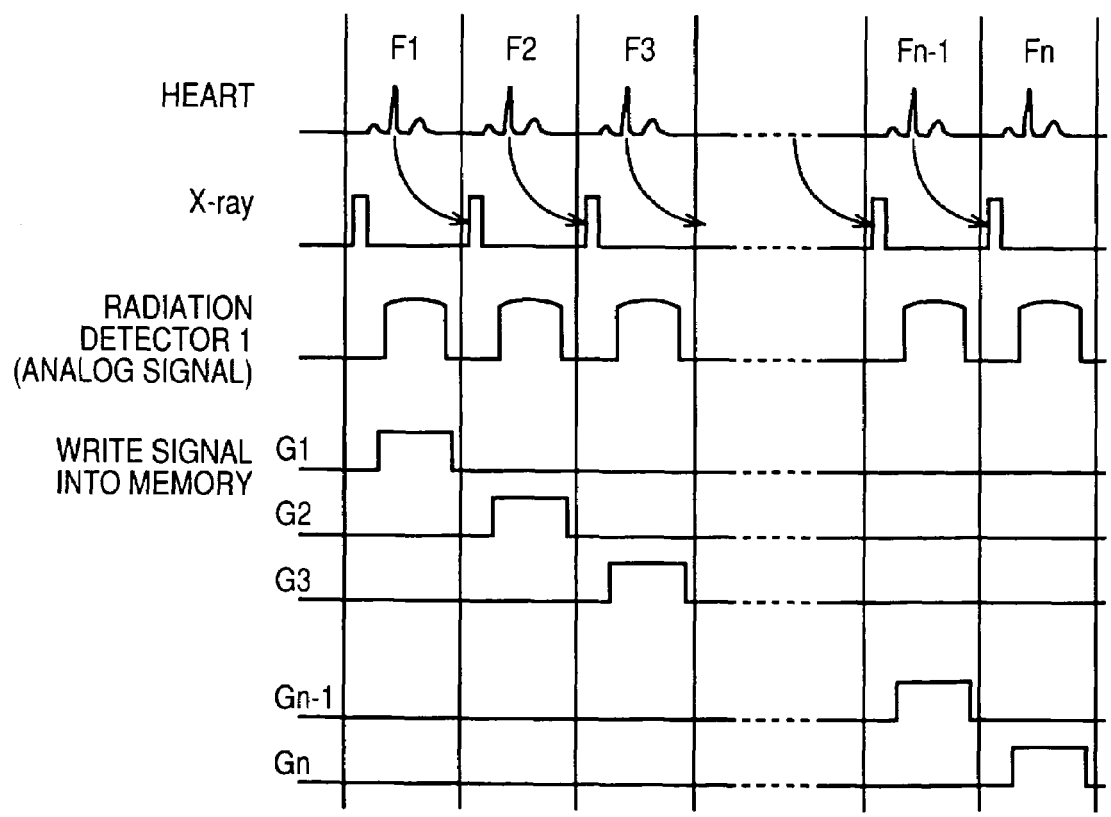
FIG. 14 is a timing chart showing a preferable control method when obtaining an X-ray tomogram of a heart.
Figure 15:
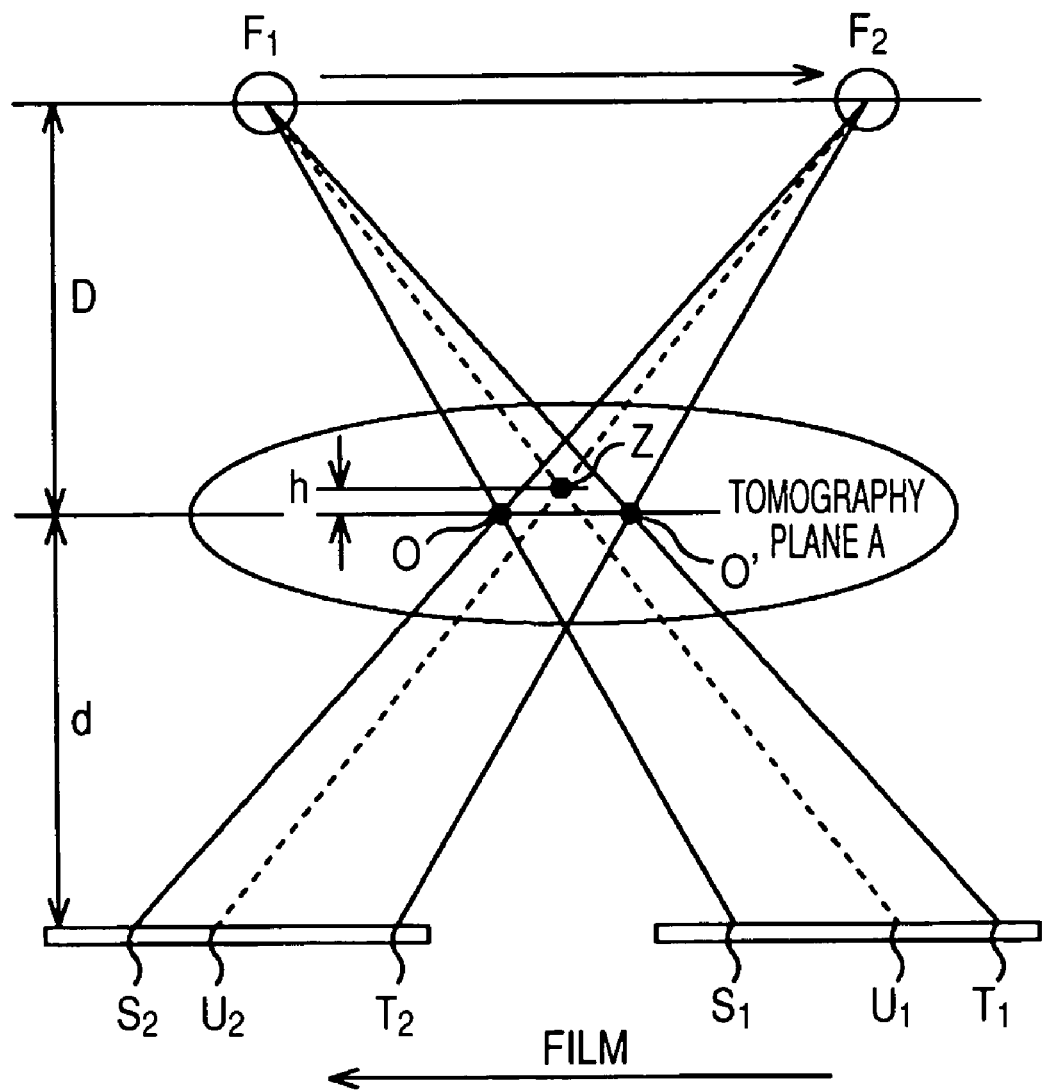
FIG. 15 is a schematic view showing a conventional tomography photographing method using a film.

To obtain an X-ray tomogram of a heart or a position nearby the heart, it is preferable to generate X rays in a period in which movement of the heart is small while detecting the movement of the heart of a patient at the state of photographing and synchronizing with the movement of the heart. FIG. 14 is a timing chart showing a control method preferable to obtain an X-ray tomogram of a heat.

As shown in FIG. 14, by considering the beat of the heart of a patient and thereby generating X rays in a period in which the movement of the heart is small, it is possible to obtain a tomogram not influenced by the movement of the heart. Particularly, because it is possible to clearly sample the information on positions nearby a heart, the diagnosis efficiency is improved.

In this case, to detect the beat of the heart, it is allowed to detect the beat by a method for obtaining a normal electrocardiogram or detect a pressure so as to measure a blood pressure.

There are several methods for detection the beat of a heart. For example, there is a measuring method referred to as the most-general twelve-induction electrocardiogram used for medical checkup. In the case of this method, a change (electrocardiogram) of a slight active current generated whenever the muscle of a heart is contracted is detected by using a plurality of electrodes set to the surface of a human body.

In the case of this method, electrodes are generally set to right and left wrists, four places of ankles and six places of the chest portion around a heart. Because many electrical wirings are used, the wirings become members for interrupting X rays when photographing an X-ray tomography image and become a disadvantage that an accurate image may not be obtained. Moreover, there is a disadvantage that electrode setting requires a lot of time.

Moreover, as another method for detecting the heart rate of a heart, there is a method for detecting a pressure for measuring a blood pressure (pressure difference between blood vessels). In the case of this method, it is allowed to set a pressure sensor to an upper arm or a finger. However, when detecting the pressure by the pressure sensor, a delay occurs at the signal peak position of the pressure sensor to the movement of the heart. Therefore, it is preferable to correct the delay and emit X rays at a point where the movement of the heart is minimized. Because the delay value slightly depends on a person, it is difficult to estimate the delay time at which the movement of the heart is minimized.

As still another method for detecting the heart rate of a heart, there is a method for detecting cardiac sound. In the case of this method, the cardiac sound is detected by bringing a probe having a built-in microphone into contact with the chest portion of a patient. When the microphone can be brought into a high sensitivity, it is possible to detect the cardiac sound by bringing the probe into contact with not only the left chest portion nearby the heart but also a separate portion. It is also possible to send a picked-up signal to a separate device through a wireless structure and a very small lightweight heart-rate detection sensor is realized.

Moreover, as still another method for detecting the heart rate of a heart, there is a method for detecting a pulse wave (change of blood-vessel volumes). The pulse wave is a wave obtaining a volume change generated due to blood incoming into a portion where there is a system of a body as a waveform from the surface of a human body, which is a blood movement reaction as it were. The blood movement reaction does not correspond to the movement of a heart one to one. By measuring the movement of a peripheral vessel, the information indirectly having the same meaning as the interval between heart rates of an electrocardiogram is obtained. As one of methods for detecting a pulse wave, there is a method for irradiating the skin surface with near-infrared light to detect a transmitted light or reflected light by a photodetector. By using that the transmitted light or reflected light is changed due to the flow rate of blood flowing through a measuring portion, a change of the flow rates of blood is converted into an electrical signal. As a measuring portion, a finger tip or ear lobule is frequently selected. Also for a method for detecting a pulse wave, it is preferable to emit X rays when the movement of heart is minimized while getting control of a time relation between a detection signal and the timing at which the movement of a heart is minimized similarly to the method for detecting a pulse wave by a pressure sensor.

Furthermore, to obtain an X-ray tomogram of a lung or a portion nearby the lung, it is preferable to synchronize generation of X rays with breathing of a patient instead of the beat of the heart of the patient. That is, X rays are generated in a period when the movement of the chest is small. By performing the above control, a high-quality chest tomography image is obtained. In this case, as a result of comparison with the beat of a heart, a lot of time is required for photographing because the cycle of breathing is long. Moreover, it is allowed to synchronize X rays with both movements of breathing and the heart.

As a method for detecting the breathing of a patient, there are a method for detecting inspired air due to breathing or inspired air set to a position nearby the cavity of nose of a patient and a method for detecting breathing sound by setting a microphone to the bronchi or lung field of a patient.

The embodiment of the present invention can be realized when a computer executes a program. Moreover, it is possible to apply means for supplying a program to a computer, for example, a computer-readable recording medium such as a CD-ROM recording the program or a transmission medium such as Internet for transmitting the program as an embodiment of the present invention. Furthermore, it is possible to apply the program as an embodiment of the present invention. The above program, recording medium, transmission medium and program product are included in the category of the present invention.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2003-354158 filed Oct. 14, 2003, and No. 2004-171226 filed Jun. 9, 2204, which are hereby incorporated by reference herein.

What is claimed is:

1. A radiation image pick-up device comprising:

radiation generation means;

radiation detection means in which a plurality of radiation detection elements for respectively converting a radiation from the radiation generation means into an electrical signal are arranged in a matrix to detect radiation;

read means for reading the electrical signal from the radiation detection means one frame by one frame for a plurality of frames;

storage means for storing data corresponding to the electrical signal read by the read means, as information groups of m frames such that one group corresponds to one frame;

position control means for controlling a position of the radiation generation means and the radiation detection means, such that, when the radiation detecting means detects radiation for m frames and a first plane is set within an object to be detected disposed between the radiation generation means and the radiation detection means, the position control means moves the radiation generation means by a moving distance Lx(m) along a second plane spaced by distance D from the first plane, and moves the radiation detection means along a third plane spaced by distance d from the first plane, and such that an intersection point between a straight line between a point at which a first one of said radiation detection elements is located and a point at which the radiation generation means is located, and the first plane is substantially at a fixed point over the m frames; and signal processing means for processing to obtain a tomography image along a fourth plane spaced from the first plane by a distance h in a direction of a side of the radiation generation means, based on the information groups of m frames, wherein the signal processing means performs the processing based on data of the first one of said radiation detection elements in an information group of a first one of the m frames, and based on data of the radiation detection element nearest to a position displaced by Zx(m) from the first one of said radiation detection elements in the information group of m-th one of the m frames, to meet a relation:

$$Z_x(m) = \frac{h \times (D+d)}{D \times (D-h)} \times L_x(m).$$

2. The radiation image pick-up device according to claim 1, wherein the signal processing means performs, as the processing, an averaging based on the information groups of m frames, wherein the signal processing means performs the processing based on data of the first one of said radiation detection elements in an information group of a first one of the m frames, and based on data of the radiation detection element nearest to a position displaced by Zx(m) from the first one of the first one of said radiation detection elements in the information group of m-th one of the m frames.

3. The radiation image pick-up device according to claim 1, wherein
movements of the radiation generation means and the radiation detection means are interrupted whenever the radiation generation means generates radiation and the radiation detection elements respectively convert radiation into an electrical signal.

4. The radiation image pick-up device according to claim 1, wherein
when the object to be detected is an animal, the radiation generation means pulsatively generates radiation by synchronizing the radiation with at least either of a beat of a heart and breathing of the animal.

5. The radiation image pick-up device according to claim 4, wherein
at least two electrodes are set on a surface of a body of the animal, and wherein the beat of the heart is detected in accordance with a change of active currents generated whenever a muscle of the heart contracts and radiation is synchronized with a signal of the beat.

6. The radiation image pick-up device according to claim 4, wherein
a pressure sensor is set on an arm, foot or finger of the animal, and wherein the beat of the heart is detected in accordance with a pressure difference between blood vessels generated whenever a muscle of the heart contracts and radiation is synchronized with a signal of the beat.

7. The radiation image pick-up device according to claim 4, wherein
a probe having a built-in microphone is set on a chest of the animal or a position nearby the chest, and wherein the beat of the heart is detected in accordance with a cardiac sound generated whenever a muscle of the heart contracts and radiation is synchronized with a signal of the beat.

8. The radiation image pick-up device according to claim 4, wherein
the beat of the heart is detected in accordance with a change of blood-vessel volumes generated when blood of the animal comes in and radiation is synchronized with a signal of the beat.

9. The radiation image pick-up device according to claim 4, wherein
a wind pressure sensor or temperature sensor that detects expiration and inspiration is set in the nasal cavity of the animal or a position nearby a nasal cavity, and wherein a breathing state of the animal is detected and radiation is synchronized with a detection signal of the breathing state.

10. The radiation image pick-up device according to claim 4, wherein
a probe having a built-in microphone is set on a bronchus or lung filed of the animal or a position nearby the bronchus or lung filed, and wherein a breath sound of the animal is detected and radiation is synchronized with a detection signal of the breath sound.

11. The radiation image pick-up device according to claim 1, wherein
the radiation detection elements respectively have a wavelength conversion body for converting radiation into visible light and a photoelectric conversion body for receiving visible light and converting the visible light into an electrical signal.

12. The radiation image pick-up device according to claim 11, wherein
the wavelength conversion body is constituted by using at least one type of material selected from a group of Gd2O3, Gd2O2S, and CsI as a material.

13. The radiation image pick-up device according to claim 11, wherein
the photoelectric conversion body is constituted by using amorphous silicon as a main material.

14. The radiation image pick-up device according to claim 1, wherein
the radiation detection elements respectively contain at least one type of material selected from a group of selenium, gallium arsenide, silver iodide, and lead iodide, absorbed radiation, and convert the radiation into an electrical signal.

15. The radiation image pick-up device according to claim 1, wherein
the radiation detection elements respectively have a switching element.

16. A radiation image pick-up method using a radiation image pick-up device having radiation generation means, radiation detection means constituted by arranging a plurality of radiation detection elements for respectively converting radiation from the radiation generation means into an electrical signal in a matrix to detect radiation and read means for reading an electrical signal from the radiation detection means one frame by one frame for a plurality of frames, comprising:
storing data corresponding to the electrical signal read by the read means, as information groups of m frames such that one group corresponds to one frame;
a step of controlling a position of the radiation generation means and the radiation detection means, so that, when the radiation detection means detects radiation for m frames and a first plane is set within an object to be detected disposed between the radiation generation means and the radiation detection means, the radiation generation means is moved a distance Lx(m) along a second plane spaced by a distance D from the first plane, and the radiation detection means is moved along a third plane spaced by a distance d from the first plane, and so that an intersection point between a straight line between a point at which a first one of said radiation detection elements is located and a point at which the radiation generation means is located, and the first plane is substantially at a fixed point over the m frames; and
a step of processing to obtain a tomography image along a fourth plane spaced from the first plane by a distance h in a direction of a side of the radiation generation means, based on the information groups of m frames, wherein the processing is based on data of the first one of said radiation detection elements in an information group of a first one of the m frames, and based on data of the radiation detection element nearest to a position displaced by Zx(m) from the first one of said radiation detection elements in the information group of m-th one of the m frames, to meet a relation:

$$Z_x(m) = \frac{h \times (D+d)}{D \times (D-h)} \times L_x(m).$$

17. A radiation image pick-up method comprising:
a step of applying radiation to an object to be detected from radiation generation means,
detecting the radiation passing through the object to be detected by arranging a plurality of radiation detection elements for respectively converting the radiation from the radiation generation means into an electrical signal in a matrix,
a step providing position control means configured to control a position of the radiation generation means and the radiation detection means,
such that, when the radiation detecting means detects radiation for m frames and a first plane is set within an object to be detected disposed between the radiation generation means and the radiation detection means, the position control means moves the radiation generation means by a moving distance Lx(m) along a second plane spaced by distance D from the first plane, and moves the radiation detection means along a third plane spaced by distance d from the first plane,
and such that an intersection point between a straight line between a point at which a first one of said radiation detection elements is located and a point at which the radiation generation means is located, and the first plane is substantially at a fixed point over the m frames; and
a signal processing step for processing to obtain a tomography image along a fourth plane spaced from the first plane by a distance h in a direction of a side of the radiation generation means, based on information groups of m frames, wherein the processing is based on data of the first one of said radiation detection elements in an information group of a first one of the m frames, and based on data of the radiation detection element nearest to a position displaced by Zx(m) from the first one of said radiation detection elements in the information group of m-th one of the m frames, to meet a relation:

$$Z_x(m) = \frac{h \times (D+d)}{D \times (D-h)} \times L_x(m).$$

18. A computer-readable recording medium encoded with a program for making a computer control a radiation image pick-up device in which an object to be detected is set between radiation generation means and radiation detection means and which has radiation generation means, radiation detection means constituted by arranging a plurality of radiation detection elements for respectively converting radiation from the radiation generation means into an electrical signal in a matrix to detect radiation, read means for reading an electrical signal from the radiation detection means, storage means for storing an electrical signal read by the read means and signal processing means for processing electrical signals stored in the storage means, which makes the computer execute:
a step of controlling a position of the radiation generation means and the radiation means, so that, when the radiation detection means detects radiation for m frames and a first plane is set within an object to be detected disposed between the radiation generation means and the radiation detection means the radiation generation means is moved a distance Lx(m) along a second plane spaced by a distance D from the first plane, and the radiation detection means is moved along a third plane spaced by a distance d from the first plane, and so that an intersection point between a straight line between a point at which a first one of said radiation detection elements is located and a point at which the radiation generation means is located, and the first plane is substantially at a fixed point over the m frames; and
a step of processing to obtain a tomography image along a fourth plane spaced from the first plane by a distance h in a direction of a side of the radiation generation means, based on information groups of m frames, wherein the processing is based on data of the first one of said radiation detection elements in an information group of a first one of the m frames, and based on data of the radiation detection element nearest to a position displaced by Zx(m) from the first one of said radiation detection elements in the information group of m-th one of the m frames, to meet a relation:

$$Z_x(m) = \frac{h \times (D+d)}{D \times (D-h)} \times L_x(m).$$

19. A computer-readable recording medium encoded with a program for making a computer execute a step of applying radiation to an object to be detected from radiation generation means and detecting the radiation passing through the object to be detected by using radiation detection means constituted by arranging a plurality of radiation detection elements for respectively converting the radiation from the radiation generation means into an electrical signal in a matrix, which makes the computer execute:
a step of controlling a position of the radiation generation means and the radiation detection means, so that, when the radiation detection means detects radiation for m frames and a first plane is set within an object to be detected disposed between the radiation generation means and the radiation detection means the radiation generation means is moved a distance Lx(m) along a second plane spaced by a distance D from the first plane, and the radiation detection means is moved along a third plane spaced by a distance d from the first plane, and so that an intersection point between a straight line between a point at which a first one of said radiation detection elements is located and a point at which the radiation generation means is located, and the first plane is substantially at a fixed point over the m frames; and
a step of processing to obtain a tomography image along a fourth plane spaced from the first plane by a distance h in a direction of a side of the radiation generation means, based on information groups of m frames, wherein the processing is based on data of the first one of said radiation detection elements in an information group of a first one of the m frames, and based on data of the radiation detection element nearest to a position displaced by Zx(m) from the first one of said radiation detection elements in the information group of m-th one of the m frames, to meet a relation:

$$Z_x(m) = \frac{h \times (D+d)}{D \times (D-h)} \times L_x(m).$$

* * * * *

UNITED STATES PATENT AND TRADEMARK OFFICE
CERTIFICATE OF CORRECTION

PATENT NO. : 7,313,219 B2
APPLICATION NO. : 10/961082
DATED : December 25, 2007
INVENTOR(S) : Tadao Endo It is certified that error appears in the above-identified patent and that said Letters Patent is hereby corrected as shown below:

<u>COLUMN 2</u>

Line 5, "objects" should read --object--; and
Line 59, "preferably" should read --preferable--.

<u>COLUMN 3</u>

Line 9, "iimage" should read --image--.

<u>COLUMN 4</u>

Line 48, "objects" should read --object--; and
Line 67, "preferably" should read --preferable--.

<u>COLUMN 5</u>

Line 34, "iimage" should read --image--;
Line 38, "sowing" should read --showing--; and
Line 46, "sowing" should read --showing--.

<u>COLUMN 7</u>

Line 21, "pixel" should read --pixels--; and
Line 40, "wirings" should read --wiring--.

<u>COLUMN 8</u>

Line 3, "are formed" should be deleted.

<u>COLUMN 9</u>

Line 1, "s-3-3" should read --S3-3--;
Line 2, "quality" should read --quantity--; and
Line 38, "amplifies" should read --amplifiers--.

<u>COLUMN 10</u>

Line 59, "in" should be deleted.

UNITED STATES PATENT AND TRADEMARK OFFICE
CERTIFICATE OF CORRECTION

PATENT NO. : 7,313,219 B2
APPLICATION NO. : 10/961082
DATED : December 25, 2007
INVENTOR(S) : Tadao Endo It is certified that error appears in the above-identified patent and that said Letters Patent is hereby corrected as shown below:

COLUMN 11

Line 6, "frames)" should read --frames).--; and
    Line 55, "descried" should read --described--.

COLUMN 12

Line 9, "E1" should read --$E_1$--; and
    Line 66, "E1" should read --$E_1$--.

COLUMN 13

Line 58, " $\overline{Q_0Q_1} = \overline{P_0P_1} = \overline{Q_2Q_3} = \overline{P_2P_3}$ " should read -- $\overline{Q_0Q_1} = \overline{P_0P_1} = \overline{Q_2Q_3} = \overline{P_2P_3}$ (Numerical Formula 14)--; and
    Line 66, "(pixel)" should read --(pixels)--.

COLUMN 16

Line 26, "heat." should read --heart.--; and
    Line 38, "detection" should read --detecting--.

COLUMN 18

Line 3, "Jun. 9, 2004," should read --June 9, 2004,--.

COLUMN 19

Line 56, "filed" should read --field--; and
    Line 57, "filed," should read --field,--.

COLUMN 20

Line 5, "Gd2O3, Gd2O2S," should read --$Gd_2O_3, Gd_2O_2S$,--.

UNITED STATES PATENT AND TRADEMARK OFFICE
CERTIFICATE OF CORRECTION

PATENT NO.       : 7,313,219 B2
APPLICATION NO.  : 10/961082
DATED            : December 25, 2007
INVENTOR(S)      : Tadao Endo It is certified that error appears in the above-identified patent and that said Letters Patent is hereby corrected as shown below:

<u>COLUMN 21</u>

Line 9, "step" should read --step of--; and
Line 64, "detection means" should read --detection means,--.

Signed and Sealed this

Thirtieth Day of September, 2008

JON W. DUDAS
*Director of the United States Patent and Trademark Office*